United States Patent
Olde et al.

(10) Patent No.: US 10,478,076 B2
(45) Date of Patent: *Nov. 19, 2019

(54) MONITORING A PROPERTY OF THE CARDIOVASCULAR SYSTEM OF A SUBJECT

(75) Inventors: Bo Olde, Lund (SE); Kristian Solem, Kavlinge (SE)

(73) Assignee: Gambro Lundia AB, Lund (SE)

( * ) Notice: Subject to any disclaimer, the term of this patent is extended or adjusted under 35 U.S.C. 154(b) by 957 days.

This patent is subject to a terminal disclaimer.

(21) Appl. No.: 13/519,532

(22) PCT Filed: Dec. 22, 2010

(86) PCT No.: PCT/EP2010/070551
§ 371 (c)(1),
(2), (4) Date: Sep. 12, 2012

(87) PCT Pub. No.: WO2011/080189
PCT Pub. Date: Jul. 7, 2012

(65) Prior Publication Data
US 2013/0023776 A1    Jan. 24, 2013

Related U.S. Application Data

(60) Provisional application No. 61/290,306, filed on Dec. 28, 2009.

(30) Foreign Application Priority Data

Dec. 28, 2009  (SE) ..................... 0951027

(51) Int. Cl.
*A61B 5/0215*   (2006.01)
*A61B 5/00*     (2006.01)
*A61M 1/36*     (2006.01)

(52) U.S. Cl.
CPC .......... *A61B 5/0215* (2013.01); *A61B 5/7203* (2013.01); *A61B 5/7264* (2013.01);
(Continued)

(58) Field of Classification Search
None
See application file for complete search history.

(56) References Cited

U.S. PATENT DOCUMENTS 3,731,680 A * 5/1973 Wright ................ A61M 1/3639
128/DIG. 3
3,882,861 A * 5/1975 Kettering ............ A61M 1/1086
128/DIG. 12

(Continued)

FOREIGN PATENT DOCUMENTS

EP    3178387    6/2014
WO    97/10013   3/1997

(Continued)

OTHER PUBLICATIONS

Acar, "Automatic ectopic beat elimination in short-term heart rate variability measurement," Computer Methods and Programs in Biomedicine, 63 (2000), pp. 123-131.

(Continued)

*Primary Examiner* — Michael R Bloch
(74) *Attorney, Agent, or Firm* — K&L Gates LLP

(57) ABSTRACT

A device is configured to monitor a cardiovascular property of a subject. The device obtains measurement data from a primary pressure wave sensor arranged to detect pressure waves in an extracorporeal fluid circuit in fluid communication with the cardiovascular system of the subject. The device has a signal processor configured to generate a time-dependent monitoring signal based on the measurement data, such that the monitoring signal comprises a sequence of heart pulses, wherein each heart pulse repre- (Continued)

sents a pressure wave originating from a heart beat in the subject; determine beat classification data for each heart pulse in the monitoring signal; and calculate, based at least partly on the beat classification data, a parameter value indicative of the cardiovascular property. The beat classification data may distinguish between heart pulses originating from normal heart beats and heart pulses originating from ectopic heart beats. The cardiovascular property may be an arterial status of the cardiovascular system, a degree of calcification in the cardiovascular system, a status of a blood vessel access used for connecting the extracorporeal fluid circuit to the cardiovascular system, a heart rate variability, a heart rate, a heart rate turbulence, an ectopic beat count, or an origin of ectopic beats. The device may be attached to or part of a dialysis machine.

32 Claims, 12 Drawing Sheets

(52) U.S. Cl.
CPC ........ *A61M 1/3639* (2013.01); *A61M 1/3644* (2014.02); *A61M 1/3646* (2014.02); *A61M 1/3656* (2014.02); *A61B 5/725* (2013.01); *A61B 5/7257* (2013.01); *A61M 1/3643* (2013.01); *A61M 2205/3331* (2013.01); *A61M 2230/06* (2013.01)

(56) References Cited

U.S. PATENT DOCUMENTS

| | | | |
|---|---|---|---|
| 4,519,395 A | 5/1985 | Hrushesky | |
| 5,390,679 A * | 2/1995 | Martin | 600/486 |
| 5,817,027 A | 10/1998 | Arand et al. | |
| 6,623,443 B1 | 9/2003 | Polaschegg | |
| 6,718,197 B1 * | 4/2004 | Carlson | A61B 5/0468 600/515 |
| 2005/0010118 A1 * | 1/2005 | Toyoda | A61B 5/02 600/486 |
| 2006/0047193 A1 | 3/2006 | Zhang | |
| 2006/0167359 A1 | 7/2006 | Bennett et al. | |
| 2007/0023298 A1 | 2/2007 | Mackenzie | |
| 2007/0215545 A1 * | 9/2007 | Bissler | A61M 1/16 210/646 |
| 2007/0232980 A1 * | 10/2007 | Felt | A61M 1/0209 604/6.1 |
| 2010/0099995 A1 * | 4/2010 | Lian | A61N 1/3702 600/515 |

FOREIGN PATENT DOCUMENTS

| | | | |
|---|---|---|---|
| WO | 2006/031186 | 3/2006 | |
| WO | WO 2006031186 A1 * | 3/2006 | ............ A61B 5/021 |
| WO | 2009/124187 | 10/2009 | |
| WO | 2009/127683 A1 | 10/2009 | |
| WO | 2009/156174 | 12/2009 | |
| WO | 2009/156175 | 12/2009 | |

OTHER PUBLICATIONS

Suhrbier, "Comparison of three methods for beat-to-beat-interval extraction from continuous blood pressure and electrocardiogram with respect to heart rate variability analysis," Biomed Tech 2006; 51: pp. 70-76.

International Search Report dated Apr. 19, 2011.

"An Electrocardiogram-Based Method for Early Detection of Abrupt Changes in Blood Pressure During Hemodialysis", Kristian Solem et al., ASAIO Journal 2006, pp. 282-290.

\* cited by examiner

US 10,478,076 B2

MONITORING A PROPERTY OF THE CARDIOVASCULAR SYSTEM OF A SUBJECT

RELATED APPLICATION

This is a U.S. National Phase of PCT/EP2010/070551 having an international filing date of Dec. 22, 2010, which designated the U.S and claims priority to U.S. Provisional Application 61/290,306 filed Dec. 28, 2009, and Swedish application 0951027-2 filed Dec. 28, 2009, the entirety of each of these applications are incorporated by reference.

TECHNICAL FIELD

The present invention generally relates to techniques for monitoring one or more properties of the cardiovascular system of a subject. The present invention is e.g. applicable in arrangements for extracorporeal blood treatment.

BACKGROUND ART

It is known in the art to measure different properties of the cardiovascular system of a human or animal subject. However, known techniques require installation of separate and specialized instruments and sensors for measuring a particular property.

SUMMARY

It is an object of the invention to at least partly overcome one or more limitations of the prior art. Specifically, it is an object to provide an alternative or complementary technique for monitoring a cardiovascular property of a subject connected to an apparatus for extracorporeal blood treatment.

This and other objects, which will appear from the description below, are at least partly achieved by means of devices, an apparatus for blood treatment, a method, and a computer-readable medium according to the independent claims, embodiments thereof being defined by the dependent claims.

A first aspect of the invention is a device for monitoring a cardiovascular property of a subject. The device comprises an input configured to obtain measurement data from a primary pressure wave sensor which is arranged to detect pressure waves in an extracorporeal fluid circuit which is connected in fluid communication with the cardiovascular system of the subject. The device further comprises a signal processor configured to: generate a time-dependent monitoring signal based on the measurement data, such that the monitoring signal comprises a sequence of heart pulses, wherein each heart pulse represents a pressure wave originating from a heart beat in the subject; determine beat classification data for each heart pulse in the monitoring signal; and calculate, based at least partly on the beat classification data, a parameter value indicative of the cardiovascular property.

A second aspect of the invention is a device for monitoring a cardiovascular property of a subject. The device comprises: means for obtaining measurement data from a primary pressure wave sensor which is arranged to detect pressure waves in an extracorporeal fluid circuit which is connected in fluid communication with the cardiovascular system of the subject; means for generating a time-dependent monitoring signal based on the measurement data, such that the monitoring signal comprises a sequence of heart pulses, wherein each heart pulse represents a pressure wave originating from a heart beat in the subject; means for determining beat classification data for each heart pulse in the monitoring signal; and means for calculating, based at least partly on the beat classification data, a parameter value indicative of the cardiovascular property.

A third aspect of the invention is an apparatus for blood treatment. The apparatus comprises an extracorporeal blood flow circuit adapted for connection to the vascular system of a subject and operable to circulate blood from the subject through a blood processing device and back to the subject, and the device according to the first or second aspects.

A fourth aspect of the invention is a method for monitoring a cardiovascular property of a subject. The method comprises: obtaining measurement data from a primary pressure wave sensor which is arranged to detect pressure waves in an extracorporeal fluid circuit which is connected in fluid communication with the cardiovascular system of the subject; generating a time-dependent monitoring signal based on the measurement data, such that the monitoring signal comprises a sequence of heart pulses, wherein each heart pulse represents a pressure wave originating from a heart beat in the subject; determining beat classification data for each heart pulse in the monitoring signal; and calculating, based at least partly on the beat classification data, a parameter value indicative of the cardiovascular property.

A fifth aspect of the invention is a computer-readable medium comprising computer instructions which, when executed by a processor, cause the processor to perform the method of the fourth aspect.

Still other objectives, features, aspects and advantages of the present invention will appear from the following detailed description, from the attached claims as well as from the drawings.

BRIEF DESCRIPTION OF THE DRAWINGS

Exemplary embodiments of the invention are described in more detail with reference to the accompanying schematic drawings.

DETAILED DESCRIPTION OF EXEMPLARY EMBODIMENTS

In the following, embodiments will be described with reference to an extracorporeal blood flow circuit. In particular, exemplary embodiments for monitoring a cardiovascular property of patient connected to such a circuit are described. A description is also given of embodiments for detecting and extracting signals indicative of such a cardiovascular property. Throughout the following description, like elements are designated by the same reference signs.

I. Example of Extracorporeal Circuit

Figure 1:
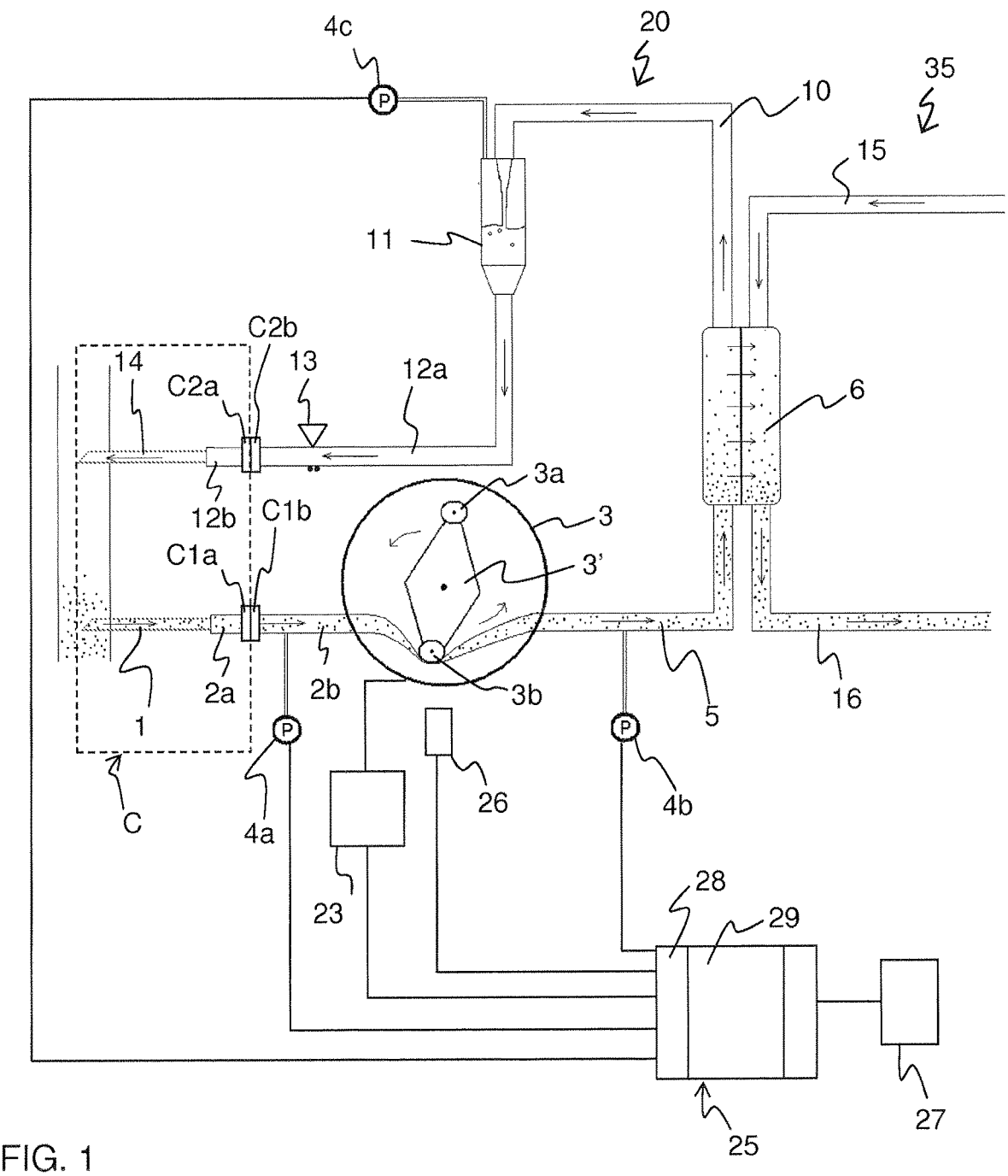
FIG. 1 is a schematic view of a system for hemodialysis treatment including an extracorporeal blood flow circuit.

FIG. 1 shows an example of an extracorporeal blood flow circuit 20, which is part of an apparatus for blood treatment, in this case a dialysis machine. The extracorporeal circuit 20 is connected to the cardiovascular system of a patient by means of a connection system C. The connection system C comprises an arterial access device 1 for blood extraction (here in the form of an arterial needle), a connection tube segment 2a and a connector C1a. The connection system C also comprises a venous access device 14 for blood reintroduction (here in the form of a venous needle), a connection tube segment 12b, and a connector C2a. The connectors C1a, C2a are arranged to provide a releasable or permanent engagement with a corresponding connector C1b, C2b in the circuit 20 so as to form a blood path between the circuit 20 and the arterial needle 1 and the venous needle 14, respectively. The connectors C1a, C1b, C2a, C2b may be of any known type.

In the illustrated example, the extracorporeal circuit 20 comprises the connector C1b, an arterial tube segment 2b, and a blood pump 3 which may be of peristaltic type, as indicated in FIG. 1. At the inlet of the pump there is a pressure sensor 4a (hereafter referred to as arterial sensor) which measures the pressure before the pump in the arterial tube segment 2b. The blood pump 3 forces the blood, via a tube segment 5, to the blood-side of a dialyser 6. In many dialysis machines, the circuit 20 is additionally provided with a pressure sensor 4b that measures the pressure between the blood pump 3 and the dialyser 6. The blood is led via a tube segment 10 from the blood-side of the dialyser 6 to a venous drip chamber or deaeration chamber 11 and from there back to the connection system C via a venous tube segment 12a and the connector C2b. A pressure sensor 4c (hereafter referred to as venous sensor) is provided to measure the pressure on the venous side of the dialyser 6. In the illustrated example, the pressure sensor 4c measures the pressure in the venous drip chamber 11. Both the arterial needle 1 and the venous needle 14 are connected to the cardiovascular system of a human or animal patient by means of a blood vessel access. The blood vessel access may be of any suitable type, e.g. a fistula, a Scribner-shunt, a graft, etc. Depending on the type of blood vessel access, other types of access devices may be used instead of needles, e.g. catheters.

Herein, the "venous side" of the extracorporeal circuit 20 refers to the part of the blood path located downstream of the blood pump 3, whereas the "arterial side" of the extracorporeal circuit 20 refers to the part of the blood path located upstream of the blood pump 3. In the example of FIG. 1, the venous side is made up of tube segment 5, the blood-side of the dialyser 6, tube segment 10, drip chamber 11 and tube segment 12a, and the arterial side is made up of tube segment 2b.

The dialysis machine also includes a dialysis fluid circuit 35, which is only partly shown in FIG. 1 and which is operated to prepare, condition and circulate dialysis fluid through the dialysis fluid-side of the dialyser 6, via tube segments 15, 16.

In FIG. 1, a control unit 23 is provided, inter alia, to control the blood flow in the circuit 20 by controlling the revolution speed of the blood pump 3.

A surveillance/monitoring device 25 is connected to the dialysis machine and configured to monitor as property of the cardiovascular system of the patient. In the example of FIG. 1, the surveillance device 25 is electrically connected to receive measurement data from one or more of the pressure sensors 4a-4c. As described in detail in the following Sections, the monitoring is based on heart pulses, which are identified in the measurement data and which are analysed for calculation of a value of one or more parameters that represent a cardiovascular property of the patient.

As indicated in FIG. 1, the device 25 may also be connected to the control unit 23. Alternatively or additionally, the device 25 may be connected to a pump sensor 26, such as a rotary encoder (e.g. conductive, optical or magnetic) or the like, for indicating the frequency and/or phase of the blood pump 3. The device 25 is tethered or wirelessly connected to a local or remote device 27 for generating an audible/visual/tactile alarm or warning signal based on calculated values (or a diagnose deduced from the calculated values), for displaying the calculated values and/or for storing the calculated values generated by the device 25. The surveillance device 25 and/or the alarm/display/storage device 27 may be incorporated as part of the dialysis machine, or be separate components.

It is to be understood that the surveillance device 25 may execute any number of other functions. The surveillance device 25 may e.g. execute safety functions, in which it acquires and analyses output signals of a number of dedicated or general sensors in the dialysis machine for identification or prevention of one or more fault conditions. One such fault condition is dislodgement of the venous or arterial access device 1, 14 from the blood vessel access, i.e. that the access device comes loose from the cardiovascular system of the patient. Another fault condition is disconnection of the venous or arterial access device 1, 14 from the circuit 20, typically by disruption/defective coupling/uncoupling of the connectors C1a, C1b and C2a, C2b, respectively.

In the example of FIG. 1, the surveillance device 25 comprises an input/output (I/O) part 28 for sampling measurement data from various sensors included in, or otherwise associated with, the dialysis machine, and for transmitting control signals to the various components included in, or otherwise associated with, the dialysis machine. The I/O part 28 may also be configured to pre-process the measurement data. For example, the I/O part 28 may include an A/D converter with a required minimum sampling rate and resolution, and one or more signal amplifiers. Generally, the measurement data is a time sequence of data samples, each representing an instantaneous sensor value. The I/O part 28 generates a number of measurement signals (e.g. one or more pressure signals), which are provided as input to a data analysis part 29 that executes the actual monitoring of the cardiovascular property. Depending on implementation, the surveillance device 25 may use digital components or analog components, or a combination thereof, for acquiring, processing and analysing the measurement data.

II. Heart Pulse Analysis

Embodiments of the invention relates to techniques for monitoring one or more properties of the cardiovascular system of a patient that is connected to an extracorporeal circuit. The cardiovascular system is the circulatory system that distributes blood in the body of patient, and is formed by the heart, the blood and the blood vessels. In the following, the monitored property is represented as a value of a cardiovascular parameter, which thus is related to a property of either the heart or the blood vessels in the patient. In certain embodiments, the parameter value may represent one or more of the arterial status (arterial stiffness) of the blood vessels, the degree of calcification of the blood vessels, and the status of the blood vessel access. In other embodiments, the parameter value may represent one of more of the heart rate variability (HRV), the heart rate (HR), the heart rate turbulence (HRT), the rate of ectopic beats (ectopic beat count, EBC), or the origin of ectopic beats (e.g. atria/ventricular).

As exemplified in FIG. 1, the extracorporeal circuit 20 may be connected to the cardiovascular system of the patient so as to circulate blood from the patient through a blood processing device 6 and back to the patient. The cardiovascular property is monitored based on a "heart pulse analysis" of a monitoring signal. The monitoring signal originates from a measurement signal which is obtained from a pressure wave sensor in (or attached to) the extracorporeal circuit. The pressure wave sensor is arranged to detect pressure waves that originate from the heartbeats of the patient. As used herein, a "pressure wave" is a mechanical wave in the form of a disturbance that travels or propagates through a material or substance. In the context of the following examples, the pressure waves propagate in the liquid system extending from the heart to the pressure wave sensor, which is in direct or indirect hydraulic contact with the liquid system, at a velocity which typically lies in the range of about 3-20 m/s. Specifically, the pressure waves propagate in the blood path that extends from the heart, through part of the cardiovascular system, the connection system C, and into the extracorporeal circuit 20.

The pressure wave sensor generates measurement data that forms a pressure pulse for each pressure wave. A "pressure pulse" is thus a set of data samples that define a local increase or decrease (depending on implementation) in signal magnitude within a time-dependent measurement signal ("pressure signal"). Correspondingly, a "heart pulse" is a pressure pulse that originates from the patient's heartbeat. Generally, the heart pulses appear at a rate proportional to the beat rate of the heart.

The pressure wave sensor may be of any conceivable type, e.g. operating by resistive, capacitive, inductive, magnetic, acoustic or optical sensing, and using one or more diaphragms, bellows, Bourdon tubes, piezo-electrical components, semiconductor components, strain gauges, resonant wires, accelerometers, etc. For example, the pressure wave sensor may be implemented as a conventional pressure sensor, a bioimpedance sensor, a photoplethysmography (PPG) sensor, etc.

In the example of FIG. 1, any one of the existing pressure sensors 4a-4c in the extracorporeal circuit 20 may be used as the pressure wave sensor.

The pressure wave sensor may also detect pressure waves that originate from other pulse generators than the patient's heart. These other pulse generators thus generate interference pulses in the pressure signal.

The interference pulses may originate from pumps and other mechanical pulse generators in the apparatus for blood treatment, e.g. in the extracorporeal circuit 20 or the dialysis fluid circuit 35. This type of interference pulses are collectively denoted "pressure artefacts" or "pump pulses" in the following description.

Figure 2:
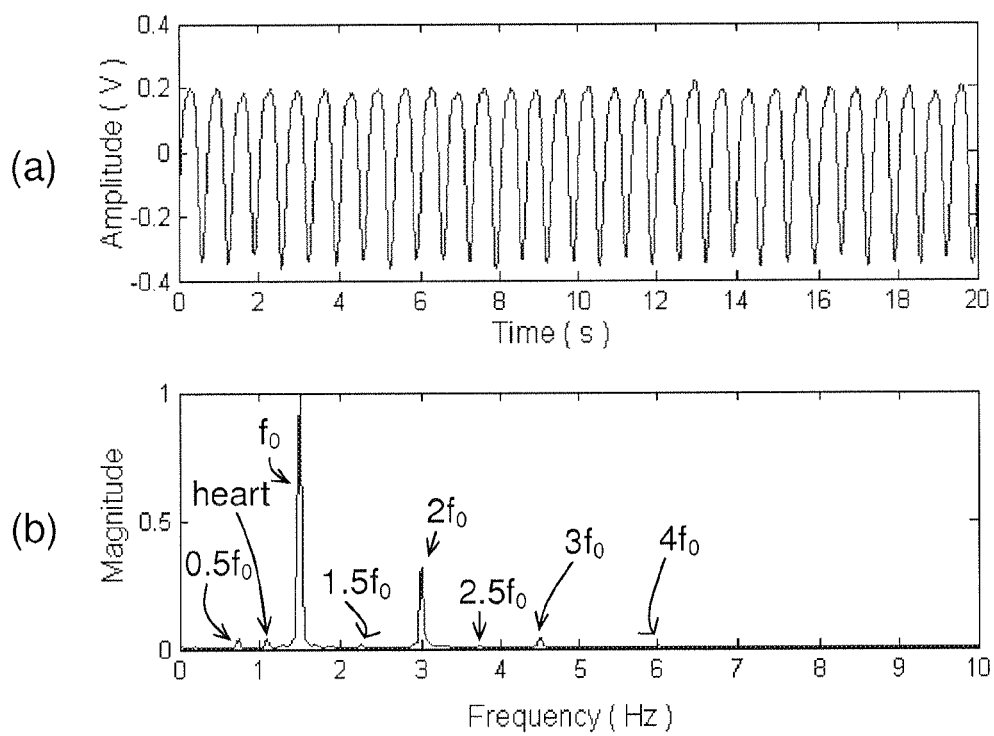
FIG. 2(a) is a plot in the time domain of a pressure signal containing both pump pulses and heart pulses.
FIG. 2(b) is a plot of the corresponding signal in the frequency domain.
Figure 9:
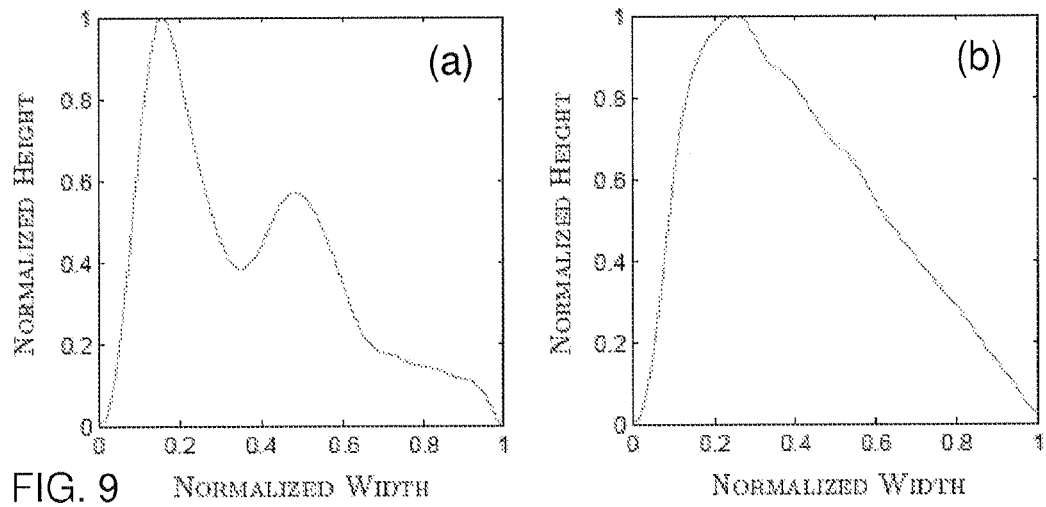
FIGS. 9(a)-9(b) are average heart pulses to illustrate the influence of arterial stiffness.

FIG. 2(a) shows an example of a pressure signal in the time domain, and FIG. 9(b) shows the corresponding energy spectral density, i.e. signal amplitude as a function of frequency. The pressure signal is obtained from the venous pressure sensor 4c in the extracorporeal circuit 20 in FIG. 1. The energy spectral density reveals that the detected pressure signal contains a number of different frequency components emanating from the blood pump 3. In the illustrated example, there is a frequency component at the base frequency ($f_0$) of the blood pump (at 1.5 Hz in this example), as well as its harmonics $2f_0$, $3f_0$ and $4f_0$. The base frequency, also denoted pumping frequency in the following, is the frequency of the pump strokes that generate pulse waves in the extracorporeal blood flow circuit. For example, in a peristaltic pump of the type shown in FIG. 1, two pump strokes are generated for each full revolution of the rotor 3', i.e. one pump stroke for each roller 3a, 3b. FIG. 2(b) also indicates the presence of a frequency component at half the pumping frequency ($0.5f_0$) and harmonics thereof, in this example at least $f_0$, $1.5f_0$, $2f_0$ and $2.5f_0$. FIG. 2(b) also shows a heart signal (at 1.1 Hz) which in this example is approximately 40 times weaker than the blood pump signal at the base frequency $f_0$. In the example of FIG. 2, the pressure signal thus contains heart pulses and pump pulses, with the latter dominating the pressure signal.

Alternatively or additionally, the interference pulses may originate from one or more physiological phenomena in the patient's body (other than the heart). Such physiological phenomena may be occasional, repetitive or cyclical (i.e. periodic). Occasional physiological phenomena include reflexes, sneezing, voluntary muscle contractions, and non-voluntary muscle contractions. Periodic physiological phenomena include the breathing (respiration) system, the autonomous system for blood pressure regulation and the autonomous system for body temperature regulation.

As explained above, the monitoring process operates on one or more "monitoring signals". In one embodiment, the pressure signal acquired from the pressure wave sensor is used as a monitoring signal. However, if the pressure signal contains interference pulses, the monitoring signal may be obtained by processing the pressure signal to remove or at least suppress the interference pulses, while essentially retaining the heart pulses. Suitably, the signal processing results in a monitoring signal that contains heart pulses and is essentially free of interference pulses. By "essentially free" is meant that the interference pulses are removed from the pressure signal to such an extent that the heart pulses may be detected and analysed for the purpose of monitoring. Different signal processing techniques for removal/suppression of interference pulses are discussed in Sections III-V below.

Figure 3:
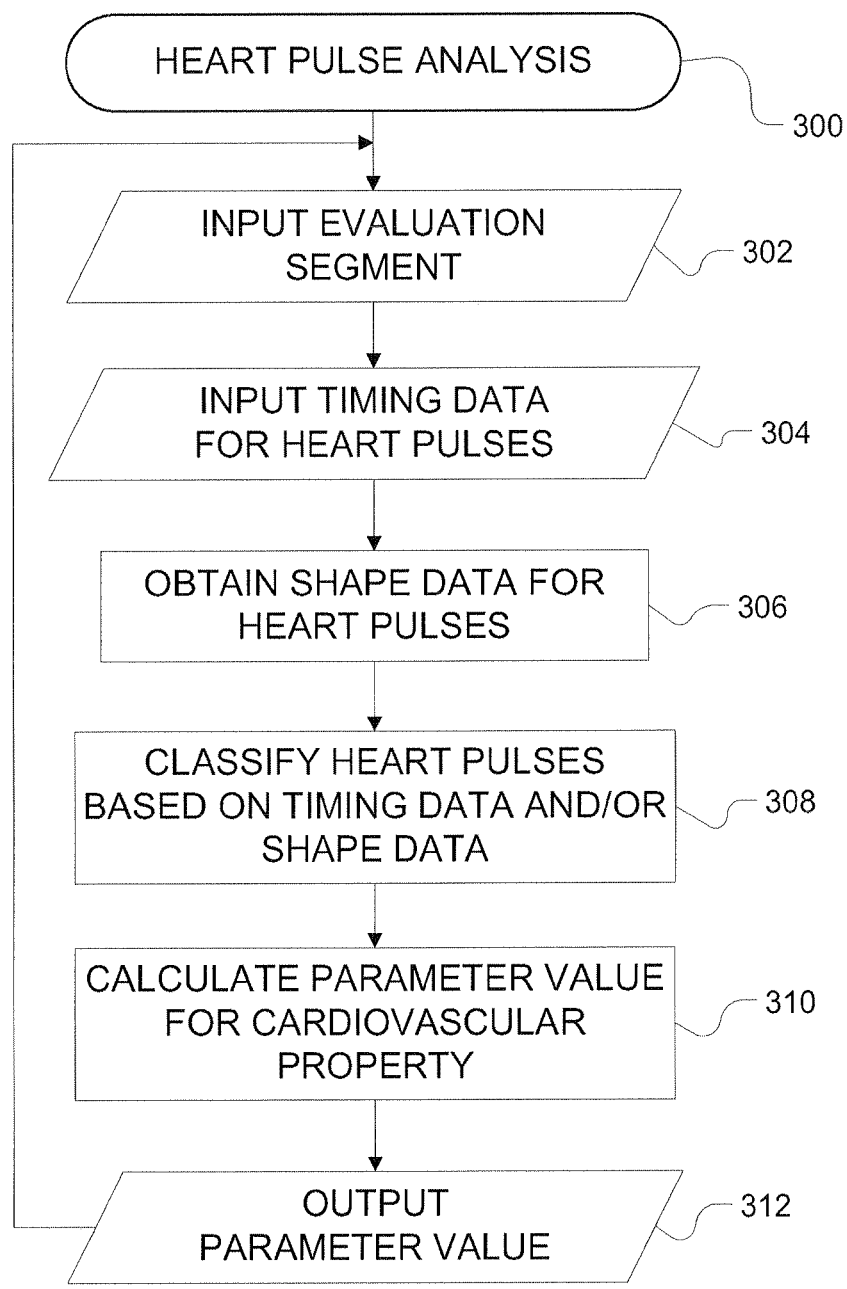
FIG. 3 is a flow chart of a process for monitoring a property of the cardiovascular system in a subject.

FIG. 3 is a flow chart of a heart pulse analysis included in an embodiment of the monitoring process. In the illustrated example, the heart pulse analysis iterates through a sequence of steps 302-312. Each iteration operates on an evaluation segment in the monitoring signal and results in a parameter value that represents a cardiovascular property of the patient. Thus, continuous monitoring (repeated iterations), typically involves calculating a time sequence of parameter values based on a time sequence of evaluation segments in the monitoring signal. The evaluation segments may be overlapping or non-overlapping in time.

In step 302, the process inputs an evaluation segment from the monitoring signal. The evaluation segment corresponds to a time window in the monitoring signal, which may be selected so as to comprise at least part of one heart pulse. In the following examples, it is assumed that the time window is selected such that each evaluation segment comprises a sequence of heart pulses, i.e. two or more heart pulses.

In step 304, the process inputs timing data (also denoted "primary timing data" herein) that indicates a time point for each heart pulse in the evaluation segment. The primary timing data may, e.g., be represented as a sequence of occurrence times for the heart pulses, or a sequence of time differences between the heart pulses. Examples of different techniques for obtaining the primary timing data is described below in Section VI.

In step 306, the evaluation segment is processed based on the primary timing data for extraction of shape data for each heart pulse in the evaluation segment. The primary timing data is used for determining the location of each heart pulse in the evaluation segment. The shape data may represent any shape feature of the heart pulse. Examples of shape features that may be extracted include the amplitude/magnitude of the heart pulse (e.g. the maximum amplitude of the pulse, or the integrated area under the pulse), the number of local maxima/minima within the heart pulse, the ratio between the amplitude of a first and a second maximum in the heart pulse (if two or more local maxima are present), a rise time of the heart pulse (e.g. time to reach maximum value), a fall time of the heart pulse (e.g. time to descend from maximum value), exponential decay of the heart pulse (e.g. given by an exponential function fitted to the trailing end of the heart pulse), the width of the heart pulse (e.g. at a given percentage of the maximum amplitude), etc. In a further variant, the shape data is a representation of the entire temporal signal profile of the heart pulse, e.g. given as a subset of the signal values in the evaluation segment, an up- or down-sampled version of these signal values, or a curve fitted to the signal values.

In step 308, each heart pulse in the evaluation segment is classified based on the shape data and/or the primary timing data. If only primary timing data is used, the preceding step 306 may be omitted. The classification aims at identifying ectopic beats among the heart pulses, i.e. to determine if each heart pulse originates from a normal heart beat or an ectopic beat (or possibly, if the heart pulse originates from neither a normal heart beat nor an ectopic beat). Thus, step 308 may result in classification data containing the beat classes: e.g. [NORMAL, ECTOPIC] or [NORMAL, OTHER] or [NORMAL, ECTOPIC, OTHER]. It is also conceivable that the classification is operable to distinguish between different types of ectopic beats, e.g. atria or ventricular, and the classification data may contain corresponding beat classes. It is to be understood that one beat class may be implicit, such that the absence of a classification for a heart pulse would imply a certain beat class of this heart pulse.

In step 310, the classification data for each heart pulse is used for calculating one or more parameter values that each represent a cardiovascular property of the patient.

In step 312, the parameter value is output and the process returns to step 302 for a new iteration.

Figure 4:
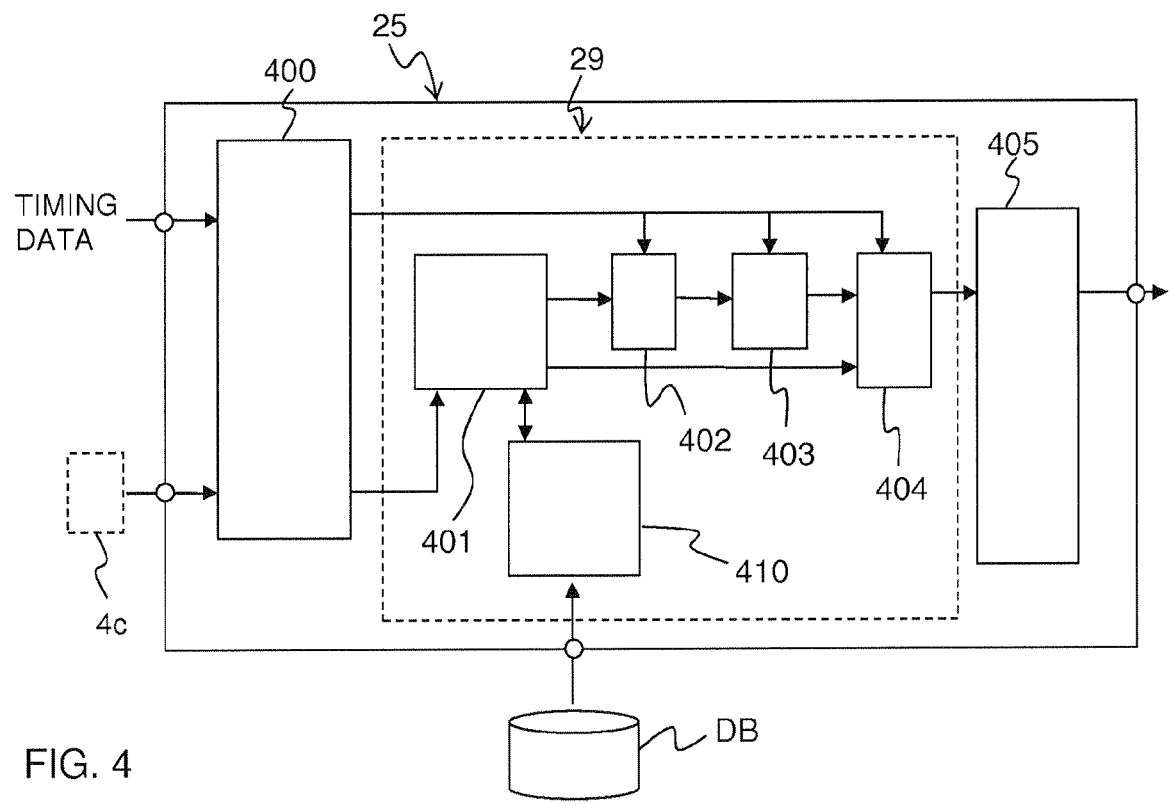
FIG. 4 is a block diagram of a surveillance device implementing the process of FIG. 3.

Embodiments of the invention also relate to the structure of a surveillance device (e.g. the device 25 in FIG. 1) that effects the monitoring. FIG. 4 is a block diagram to illustrate an embodiment of such a surveillance device 25. The device 25 includes a data acquisition part 400 which is configured to sample data from e.g. the venous pressure sensor 4c in the extracorporeal circuit 20 (FIG. 1) and to generate a pressure signal. The data analysis part 29 includes a block 401 which receives and processes the pressure signal for generation of a monitoring signal. The monitoring signal contains heart pulses and is suitably essentially free of interfering pulses (such as pump pulses and pulses from other physiological phenomena than the heart). For example, block 401 may be configured to implement any of the embodiments for signal processing described in Sections III-V below, or another signal processing. The data analysis part 29 may also includes a block 402 which sequentially obtains evaluation segments from block 401 and generates shape data for each heart pulse in the evaluation segment, e.g. according to step 306 in FIG. 3. The block 402 uses primary timing data, which (in this example) is input via the data acquisition part 400. A block 403 is configured to operate on the shape data from block 402, as well as the primary timing data, to generate classification data for each heart pulse in the evaluation segment, e.g. according to step 308 in FIG. 3. A block 404 is configured to calculate the cardiovascular parameter value based on (in this example), classification data from block 403, the evaluation segment obtained from block 401 and the primary timing data. Thus, block 404 may e.g. implement step 310 in FIG. 3. The device 25 further includes a data output part 405, which receives and outputs the parameter value. It should be understood that the parts 400 and 405 may form part of the I/O part 28 in FIG. 1. It should be emphasized that the use and flow of data in FIG. 4 is merely given for the purpose of illustration. For example, block 403 may operate on either shape data or primary timing data, or both, to generate the classification data. In another example, block 404 may operate on the shape data instead of (or in addition to) the evaluation segment, with or without access to the primary timing data, to generate the cardiovascular parameter value. In yet another example, block 404 may operate solely on the primary timing data and the classification data.

In FIG. 4, the data analysis part 29 also includes a pulse prediction block 410 which implements a step for obtaining a pulse profile which is a predicted temporal profile of pump pulses generated in the extracorporeal circuit. The pulse prediction block 410 may operate on data from a database DB (a reference library). The resulting pulse profile may be provided to block 401, which may be configured to use the pulse profile for time domain filtering, as will be explained in detail in Section III-V below.

The data analysis part 29, and thus blocks 401-404 and 410, may be implemented by software instructions that are executed by a processing device, such as a general- or special-purpose computer device or a programmed microprocessor. However, it is conceivable that some or all blocks are fully or partially implemented by dedicated hardware, such as an FPGA, an ASIC, or an assembly of discrete electronic components (resistors, capacitors, operational amplifiers, transistors, etc), as is well-known in the art. The skilled person realizes that the blocks 400-405, 410 need not retrieve/supply data directly from/to one another, but might instead store and retrieve data from an intermediate electronic storage, such as a computer memory.

In the following, different embodiments of the classification step 308 (and thus at least part of the functionality in block 403), and the parameter calculation step 310 (and thus at least part of the functionality in block 404), will be exemplified and described in further detail.

Classification of Heart Pulses (Step 308/Block 403)

The classification of the heart pulses may be done in many different ways, e.g., with the help of the primary timing data and/or the shape data.

Use of Primary Timing Data

In healthy subjects under calm conditions, variations in heart rhythm (heart rate variability, HRV) may be as large as 15%. Unhealthy subjects may suffer from severe heart conditions such as atrial fibrillation and supraventricular ectopic beating, which may lead to an HRV in excess of 20%, and ventricular ectopic beating, for which HRV may be in excess of 60%. These heart conditions are not uncommon among, e.g., dialysis patients. Thus, the labelling of different heart pulses may be based on a classification criterion involving heart rhythm.

For example, the primary timing data, which represents the occurrence times of the heart pulses, may be used to check if the time intervals between heart pulses are "normal" or "abnormal". In order to determine if a time interval is normal or abnormal, an interval-based criterion may be used, where the criterion, e.g., may be defined to classify an interval as abnormal if the interval is 20% larger than mean of the preceding intervals. If the time interval is determined as abnormal the associated heart pulse may be classified as ectopic.

Use of Shape Data

If the shape data is a representation of the entire temporal signal profile of the respective heart pulse (denoted "heart pulse profile"), each heart pulse profile may be classified as originating from a normal heart beat or an ectopic beat by matching the heart pulse profile to a set of templates. The set of templates may represent one or more temporal signal profiles (shapes) of the different beat classes, and the matching may be done using any suitable convolution method, including cross-correlation. The heart pulse profile may then be classified in one of the available beat classes based on the outcome of the matching (e.g. the maximum correlation coefficient(s)). If desired, each heart pulse profile may be subjected to linear-phase, bandpass filtering in order to remove frequencies which are less essential for classification (e.g., using a 3-dB filter with cut-off frequencies at 1 and 35 Hz, respectively). The above-mentioned templates are typically fixed and predetermined.

Since ectopic pulses may vary a lot in shape, it may be desirable to allow for the use of templates that are not fixed and predetermined. In such a variant, the heart pulse profiles are classified using a cross-correlation-based (CC) method (or any other convolution method) which involves the heart pulse profiles and a measure of the local signal-to-noise ratio (SNR) before the respective heart pulse in the evaluation segment. The CC method may be adaptive and initialized by using the first heart pulse profile in the evaluation segment as a template. Subsequently, a current heart pulse profile may be compared to the current set of templates by computing the corresponding CC coefficients, wherein each coefficient is computed by shifting the current heart pulse profile with respect to each template in the current set of templates until the best correlation is found. A new template may be created, from the current heart pulse profile, when the CC coefficient drops below an SNR-dependent threshold. The SNR may continuously be updated and measured as a root-mean-square value (or equivalent) of the high-pass filtered samples contained in an interval prior to the respective heart pulse in the evaluation segment. A heart pulse profile that is classified as being similar to a current template will update the template through averaging, e.g. using exponential averaging with a forgetting factor.

It is to be understood that only part of each heart pulse profile might be matched against the set of templates in either of the above-described variants.

If the shape data for each heart pulse contains N different shape features ($N \geq 1$), the heart pulse may be represented in an N-dimensional space spanned by the N different shape features. Different types of heart pulses (e.g. originating from a normal heart beat, different ectopic beats, and possibly other beat structures) may form distinct or at least distinguishable clusters in the N-dimensional space. Thus, the shape data of each heart pulse may define a given location in the N-dimensional space, and the heart pulse may be thus be classified based on the distance from this location to the different clusters. For example, the heart pulse may be given the classification of the nearest cluster (given by any suitable metric) in the N-dimensional space. Of course, there may be other ways to classify a heart pulse based on the shape feature(s) in the shape data, which is obvious to a person skilled in the art of, e.g., classical classification theory based on feature extraction.

The skilled person also realizes that combinations of primary timing data and shape data may be used in order to classify a heart pulse, e.g. by including the primary timing data (or a feature derived therefrom) in the N-dimensional space, or by using the primary timing data to facilitate/improve the matching or CC calculations.

Calculation of Parameter Value (Step 310/Block 404)

Figure 5:
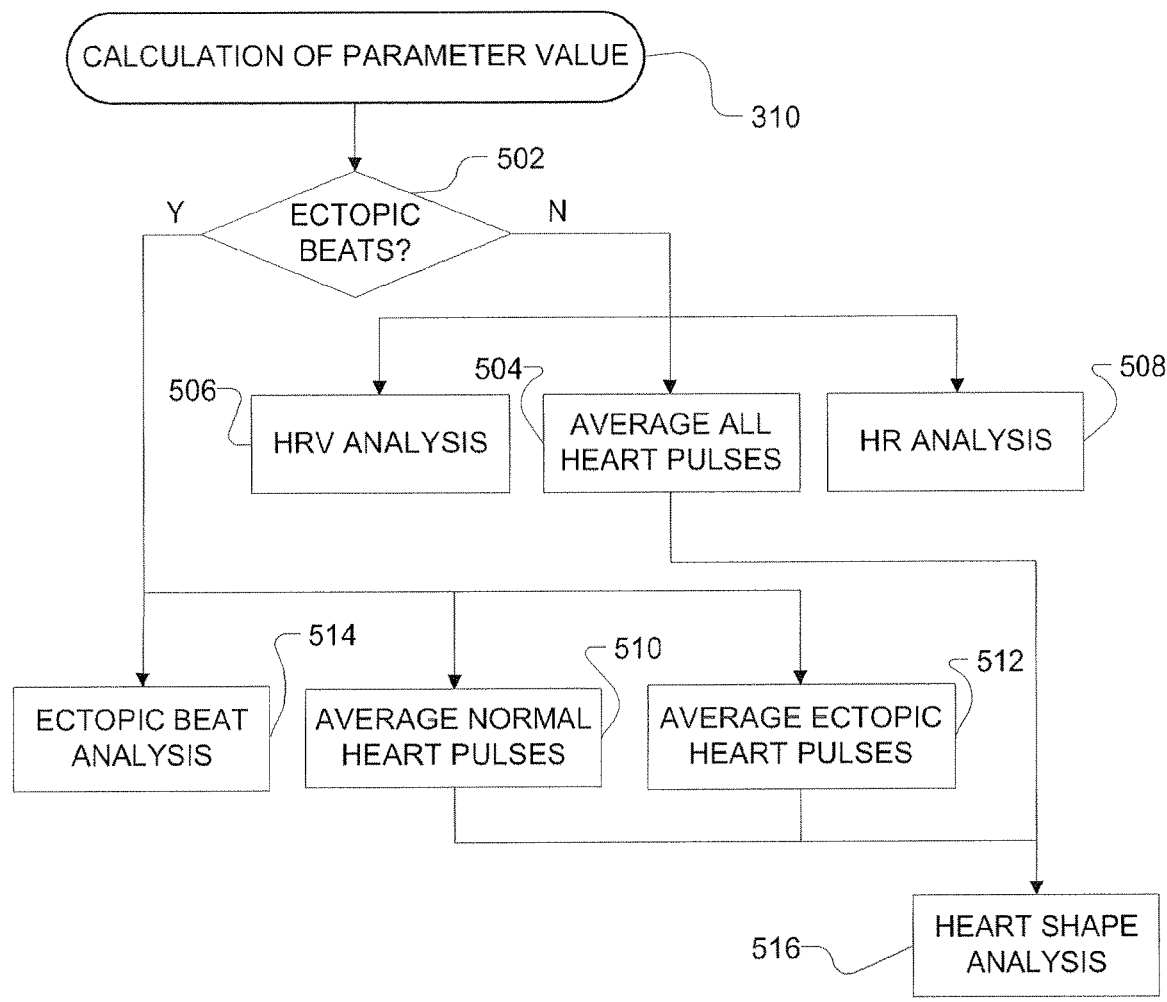
FIG. 5 is an expanded flow chart of a step included in the process of FIG. 3.

The calculation of the parameter value is further exemplified in FIG. 5 which illustrates different calculation procedures that may be executed based on the outcome of the preceding classification step (308 in FIG. 3). If the classification data indicates absence of ectopic pulses in the evaluation segment, a decision step 502 directs the calculation process to execute one or more of the calculation procedures 504, 506 and 508. If the classification data indicates presence of ectopic pulses in the evaluation segment, the calculation process is directed (in step 502) to execute one or more of calculation procedures 510, 512, 514.

Conceptually, the decision step 502 also involves a step of generating secondary timing data, which indicates the timing of heart pulses to be used in the calculation procedures 504-516. In the majority of the illustrated calculation procedures, the secondary timing data is identical to the primary timing data. In these cases, if the primary timing data has already been obtained (e.g. in step 304 in the example of FIG. 3), the primary timing data may be used as secondary timing data; otherwise the secondary timing data may be obtained according to the examples given in Section VI, if needed in a particular calculation procedure. However, in certain implementations of the calculation procedure 514, as will be described below, the secondary timing data may be generated to replace the primary timing data in the calculation of the parameter value. Since the step 310 of calculating the parameter value involves step 502, which analyses the classification data and generates the secondary timing data, it may be said that step 310 involves a preparatory step of generating secondary timing data based on the classification data irrespective of the downstream calculation procedure.

As indicated in FIG. 5, the calculation procedures 504, 510 and 512 all involve a step of averaging either normal heart pulses (procedures 504 and 510) or ectopic heart pulses (procedure 512). Such an averaging procedure may involve using the secondary timing data (and in procedure 512, the classification data) to extract a set of heart pulse segments (each typically containing a single heart pulse) from the evaluation segment, aligning the heart pulse segments in the time domain based on the secondary timing data, and generating an average representation based on the aligned signal values for each time value in the time domain. If the shape data is in the form of heart pulse profiles, these heart pulse profiles may be processed for averaging instead of the heart pulse segments. Each set of aligned signal values may e.g. be processed to generate a sum, average or median. The skilled person realizes that there are further equivalent ways to process the aligned signal values to achieve an average representation. FIG. 5 also indicates that each of the calculation procedures 504, 510 and 512 is combined with a calculation procedure 516 that performs a heart shape analysis on the average representation to generate a parameter value. It should also be understood that the average representation may be calculated repeatedly during the heart pulse analysis (cf. 300 in FIG. 3), resulting in a sequence of average representations, each resulting in a cardiovascular parameter. Any number of heart pulses (two or more) may be combined to yield the average representation. In certain embodiments, the average representation may be obtained by combining heart pulses obtained during a large part of a treatment session, e.g. during several hours.

The calculation procedure 506 involves a heart rate variability (HRV) analysis of the (normal) heart pulses in the evaluation segment. The calculation procedure 508 involves a heart rate (HR) analysis of the (normal) heart pulses in the evaluation segment. The calculation procedure 514 involves an ectopic beat analysis of the ectopic heart pulses in the evaluation segment.

Below, each of the calculation procedures 506, 508, 514 and 516 are exemplified in further detail.

HRV Analysis (Calculation Procedure 506)

Variations in heart rate are described with the widely accepted term heart rate variability (HRV). The heart rate is influenced by the parasympathetic and sympathetic activity, causing the heart rate to vary. Thus, the analysis of HRV is a useful non-invasive tool for deriving information about the state of the ANS (Autonomic Nervous System) in the patient, which information reflects the balance between parasympathetic and sympathetic activity.

There are two main approaches to characterize HRV, namely, time domain methods and frequency domain methods (also denoted spectral analysis).

Time domain methods offer a simple approach to access the autonomic tone of the heart rate. A large number of parameter values may be obtained by applying mean and standard deviation to the time difference between heart pulses (defined as RR intervals) in various ways, e.g., the standard deviation of normal-to-normal RR intervals (also known as SDNN), and the standard deviation of the 5 minute normal-to-normal RR interval mean, (also known as SDANN). Other time domain methods for calculating parameter values are based on the differences between adjacent RR intervals, such as pNN50 (the proportion of RR intervals where the difference is >50 ms) and pNN6.25% (the proportion of RR intervals where the difference is >6.25% of the mean heart period). There is a large positive correlation between many of the time domain parameters.

Other time domain methods are the so-called geometrical methods, e.g., histograms and Poincaré plots. Commonly used histograms include the sample density histogram of RR interval duration and the sample density histogram of differences between successive RR intervals. The so-called Poincaré plot analysis is a well-known non-linear time domain method to assess the dynamics of HRV. The Poincaré plot is a representation of a time series into a Cartesian plane, where each RR interval is plotted as a function of the previous RR interval. Analysis of Poincaré plots may be performed by a simple visual inspection of the shape and geometry of the plot. A quantitative analysis of the HRV may be obtained by converting the two-dimensional plot into various one-dimensional views, e.g., by fitting an ellipse to the plot shape. If this technique is applied, three popular parameter values may be obtained: the standard deviation (SD) of the instantaneous beat-to-beat RR interval variability (minor axis of the ellipse or SD1), the SD of the long term RR interval variability (major axis of the ellipse or SD2) and the axes ratio (SD1/SD2).

A simple characterization of HRV is provided by the RR interval tachogram, i.e., the RR intervals as a function of beat number. A HRV parameter value is then easily obtained from the discrete Fourier transform (DFT), since the tachogram is reviewed as a regularly sampled signal. However, the resulting spectral estimate is not expressed in terms of Hz, since the tachogram is not given in seconds. If instead the interval function is used, which is defined by the RR interval as a function of its occurrence time, it is possible to express the spectral estimate in Hz. In order to obtain the spectral estimate of the HRV, interpolation and resampling may have to be done prior to use of the DFT, since the interval function is generally an irregularly sampled signal. Alternatively, techniques for unevenly sampled signals may be employed, e.g., Lomb's method.

Another approach to derive an estimate of the HRV is based on the inverse interval function, i.e., the instantaneous heart rate (the inverse of the RR interval) as a function of its occurrence time. A continuous representation of the heart rate, i.e., the heart rate signal, may be obtained by interpolation of the inverse interval function. Resampling of the heart rate signal followed by use of the DFT yields an estimate of the HRV. The heart rate signal is commonly used in order to obtain an estimate of the HRV. A resampled version of the heart rate signal may be acquired in a fast and easy manner. Alternatively, techniques for unevenly sampled signals may be employed directly on the inverse interval function.

Yet another approach to HRV analysis is to employ model-based methods, which are based on certain physiological properties of the sinoatrial node. One such method is the heart timing (HT) signal, which is based on the well-known integral pulse frequency modulation (IPFM) model.

As noted in the foregoing, prior to performing a spectral analysis, it may be important to consider the limitations of the heart rate signal caused by the physiological properties of the heart. The heart rate is generally an unevenly sampled signal, where the heart rate itself is the sampling rate. Hence, all frequency domain methods should take aliasing into consideration, at around half the mean heart rate, at least for HRV methods that make use of the beat occurrence times. In an evaluation segment with a mean heart rate of 60 bpm, or equivalently 1 Hz, one should not analyze frequencies above 0.5 Hz. The spectrum is often divided into two sub-bands: the low frequency (LF) band (0.04-0.15 Hz) and the high frequency (HF) band (0.15-0.40 Hz). Sometimes an additional sub-band is used: the very low frequency (VLF) band (below 0.04 Hz).

Figure 7:
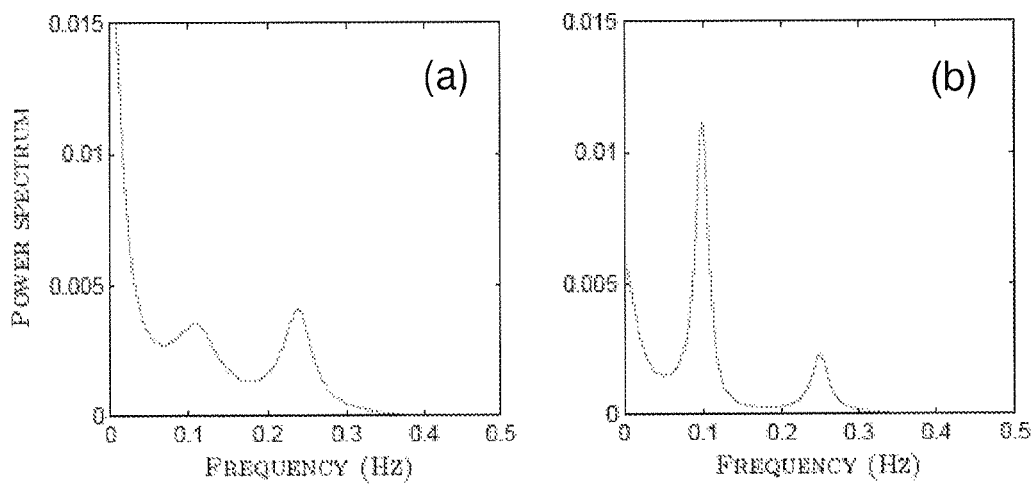
FIGS. 7(a)-7(b) are power spectra of a heart rate signal obtained from a normal subject during a resting condition and a 90 degree head-up tilt, respectively.

Respiratory activity as well as blood pressure and thermoregulation generate oscillatory behavior in the spontaneous variations in heart rate. A respiratory peak is often found in an interval ranging from 0.2-0.4 Hz, thus affecting the HF band. The LF band is affected by the baroreceptor reflex with a blood pressure peak around 0.1 Hz, and a peak from thermoregulation may be found in the VLF band. The oscillatory behavior, especially from blood pressure and thermoregulation, is sometimes less pronounced in order to render peaks in the spectra. The effect on HRV due to changes in the autonomic balance has been investigated in several studies, with the main conclusion that the LF band is influenced by sympathetic activity, whereas parasympathetic activity influences the HF band. This is further illustrated in FIG. 7, which shows a power spectrum obtained by fitting a 7th-order autoregressive (AR) model to a heart rate signal acquired from a normal subject during (a) resting conditions and (b) a 90 degree head-up tilt. The head-up tilt increases sympathetic activity as reflected by the increased peak at 0.1 Hz. The peak at 0.25 Hz may be attributed to respiration as controlled by parasympathetic activity. Thus, the spectral power ratio, the so-called LF/HF ratio, reflects autonomic balance. The total power of a spectrum equals the variance of the corresponding time domain signal, and thus correlates with the time domain variable SDNN. Furthermore, the time domain variable pNN50 is correlated with the HF power.

Heart rate variability has an important clinical significance in various medical fields, especially in the field of cardiac-related diseases. As mentioned, normal heart rate is not associated with clockwork regularity, but with variability, e.g., due to respiration, exercise, and physical or mental stress. Absence of such variability is proven to be a significant predictor of adverse outcomes following acute myocardial infarction, including all-cause mortality, ventricular fibrillation and sudden cardiac death. Heart rate variability is also markedly reduced in sudden cardiac death survivors compared with normal controls. Furthermore, it is well-known that HRV is reduced in patients with heart failure, and that HRV is altered in patients after cardiac transplantation and in other cardiovascular diseases. The clinical importance of HRV in fetal monitoring is well accepted. The HRV of the fetal heart is one of the most reliable indicators of fetal well-being, e.g., monitoring of fetal ANS development or fetal behavior states (quiet or active sleep, presence or absence of breathing movements). Heart rate variability analysis has also been utilized in noncardiac disorders that likely influence the cardiovascular system, as in diabetes patients for diagnostic purposes, and in such wide areas as ageing, Alzheimer's disease, and Chagas' disease.

Heart rate variability has been widely studied in connection with hemodialysis. Studies have shown a decrement in HRV in hemodialysis patients, and a reduced HRV may have independent prognostic value in chronic hemodialysis patients since patients with an increased risk for all-cause mortality and sudden cardiac death may be identified. Autonomic dysfunction during hemodialysis have been studied, as well as determinants of HRV in hemodialysis patients. Relationships between HRV and blood pressure during hemodialysis have also been investigated. However, little is yet known about changes in the activity of the ANS occurring just before and during a hypotensive episode. Most attention has been focused on the LF/HF ratio, in hypotension-prone and hypotension-resistant uremic patients. It has been concluded that the LF/HF ratio may be used as a marker of hypotension in hemodialysis patients, since a significant increase in the LF/HF ratio was observed during dialysis sessions without hypotension, whereas, at the time of collapse, the LF/HF ratio fell markedly in sessions with hypotension. It has also been suggested that the LF/HF ratio may reveal differences between groups with different propensity to hypotension and thus give a deeper insight into autonomic control during dialysis and provide a useful index for discriminating between hypotension prone and hypotension resistant patients.

The inventors have also realized that the HRV measure obtained via the HRV analysis in step 506 includes disturbances from pumps and other mechanical pulse generators in the apparatus for blood treatment, even if the corresponding interference pulses have been removed in the monitoring signal. The transit time of the pressure wave originating from the heart is affected by the average pressure in the blood line(s) that transmits the pressure wave. For example, since this average pressure is modulated by the pump strokes of the blood pump 3, the HRV measure may include variations in transit time caused by the operation of the pump. In one embodiment, the heart pulse analysis includes a compensation step designed wholly or partly compensate for the influence of the blood pump (and other mechanical pulse generators) on the resulting HRV measure. Such a compensation step may be implemented in many different ways.

In one embodiment, the compensation is made in the time domain, and involves adjusting the primary timing data (the occurrence times of heart pulses) which is derived from the monitoring signal. The adjustment may be done with the help of the current absolute pressure in the relevant blood line(s), e.g. obtained from any one of the pressure sensors 4a-4c. The absolute pressure affects the transit time of a pulse, thus the occurrence time may be adjusted in time, e.g. with the help of a look-up table associating absolute pressure with transit time. Following the compensation step, the HRV measure may be calculated using either a time domain or a frequency domain method.

In another embodiment, a compensation measure representing the HRV disturbance is obtained as the difference between the calculated HRV measures in a first time period while the blood pump is stopped and a second time period while the blood pump is running. Both energy/magnitude and frequency content of the HRV disturbance may be calculated. The compensation measure may e.g. be obtained at the beginning of a treatment session and/or by intermittently stopping the blood pump during a treatment session.

In another embodiment, the compensation measure is obtained in a laboratory setting, which allows heart pulses to be generated with constant rate (i.e., no HRV) while a blood pump is running. In the laboratory setting, the compensation measure may be obtained by calculating the HRV measure at different blood flows for a given constant heart rate, since the calculated HRV measure is solely caused by the blood pump. During treatment, the compensation measure is subtracted from the calculated HRV, where the compensation measure is selected based on the current blood flow rate, e.g. given by a set value of the control unit 23 (FIG. 1), or by an output signal of the pump sensor 26.

In yet another embodiment, the compensation measure is obtained during treatment as the difference between the calculated HRV measures at two different blood flow rates close in time. The similarity between the two HRV measures is the "true" HRV, and the difference is caused by the blood pump.

In a further embodiment, the compensation measure is obtained during treatment by comparing HRV measures that are calculated based on monitoring signals generated from concurrently obtained measurement data from the venous sensor 4a and the arterial sensor 4c (FIG. 1). It is understood that the blood pump will affect the transit time differently in the venous line and the arterial line, and that the difference between the HRV measures is indicative of the HRV disturbance.

In yet another embodiment, the compensation involves estimating one or more frequency bands affected by the blood pump, e.g. based on the speed of the blood pump and the current heart rate. Then, the energy in the frequency band(s) may be disregarded (suppressed) when the HRV measure is calculated using a frequency domain method.

HR Analysis (Calculation Procedure 508)

The heart rate may be calculated according to the description given above in relation to HRV analysis. The parameter value may be calculated to represent, e.g., the average heart rate over a predetermined time period (e.g. within one evaluation segment, or over a number of evaluations segments), and/or the instantaneous heart rate.

Ectopic Beat Analysis (Calculation Procedure 514)

Figure 6:
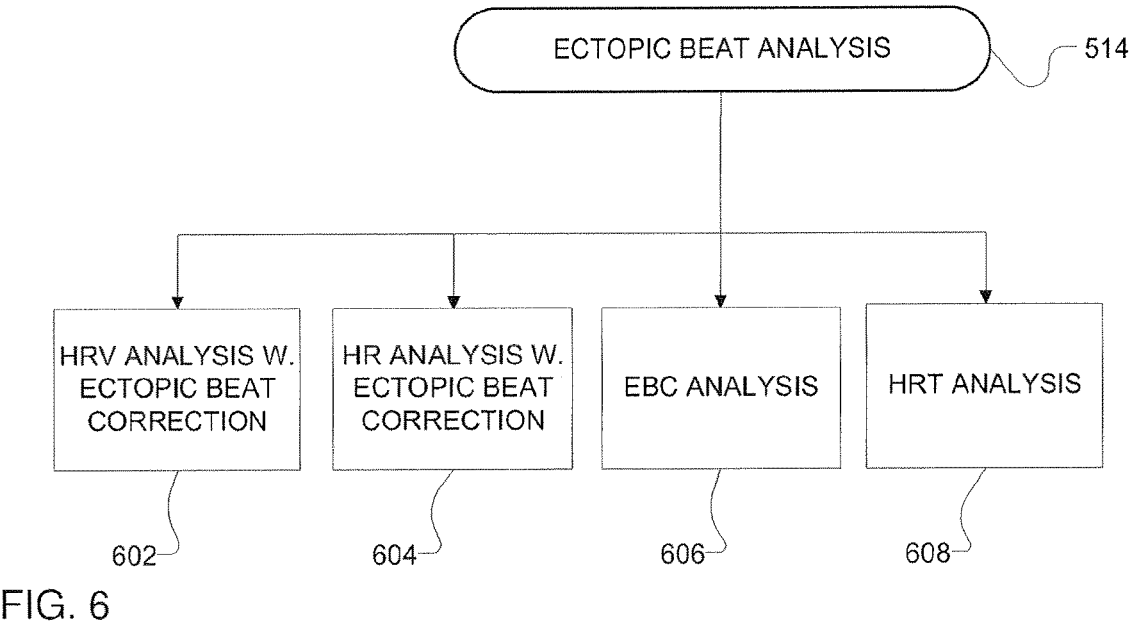
FIG. 6 is an expanded flow chart of a step included in the process of FIG. 5.

The ectopic beat analysis 514 may involve one or more calculation procedures 602, 604, 606, 608, as exemplified in FIG. 6. The calculation procedure 602 involves a process of correcting the ectopic beats in the evaluation segment, and a process of performing a heart rate variability (HRV) analysis of the heart pulses in the thus-corrected evaluation segment. The HRV analysis may be performed according to the calculation procedure 506 described above. The calculation procedure 604 also involves the process of correcting the ectopic beats in the evaluation segment, and a process of performing a heart rate (HR) analysis of the heart pulses in the thus-corrected evaluation segment. The HR analysis may be performed according to the calculation procedure 508 described above. The calculation procedure 606 involves an ectopic beat count (EBC) analysis of the ectopic pulses in the evaluation segment. The calculation procedure 608 involves a heart rate turbulence (HRT) analysis based on the ectopic pulses in the evaluation segment.

Below, the ectopic beat correction of calculation procedures 602 and 604, as well as the calculation procedures 606 and 608, are exemplified in further detail.

Ectopic Beat Correction (Calculation Procedures 602, 604)

The presence of ectopic beats perturbs the impulse pattern initiated by the sinoatrial node, thus introducing errors in HRV and HR analyses. The errors consist of impulse-like artefacts in the RR interval series, introduced by the RR intervals adjacent to an ectopic beat. Prolonged RR intervals, missed or falsely detected beats introduce similar impulse-like artefacts in the RR interval series, and implies that such RR intervals neither may be used for HRV or HR analysis. Since ectopic beats may occur in both normal subjects and patients with heart disease, their presence represents an error source which should be dealt with before spectral or time domain analysis of the heart pulses in the evaluation segment. If not dealt with, the analysis of an RR interval series containing ectopic beats may result in a power spectrum with spurious frequency components. A number of techniques have been developed which deal with the presence of ectopic beats, all techniques conforming to the restriction that only evaluation segments with occasional ectopic pulses should be processed. Evaluation segments containing frequent ectopic pulses or, worse, runs of ectopic pulses, perturb the underlying sinus rhythm and should therefore be excluded from further analysis. A simplistic approach to the correction of an occasional ectopic beat is to delete the aberrant RR intervals from the series of RR intervals. However, interval deletion does not try to fill in the interval variation that should have been present, had no ectopic beat occurred, and, as a result, the "corrected" interval series remains less suitable for HRV and HR analysis. Interval deletion may, however, be successfully employed in time domain methods, since time domain methods usually do not use variations on a beat-to-beat level.

Other techniques for ectopic beat correction strive to reproduce the interval variation that should have been present, had no ectopic beat occurred. Interpolation is often used in order to correct for the presence of ectopic beats in the non-model based methods mentioned above, e.g., the heart rate signal. In this correction technique, some kind of interpolation is performed over the gap caused by the ectopic beat in order to obtain values that align with the adjacent values of normal heart pulses. A low order interpolation is usually employed, in which interpolation is performed in an interval covering the disrupted signal values adjacent to the ectopic beat. Compensation for the presence of an ectopic beat may also be obtained in the above-mentioned IPFM-based method.

Thus, it should be understood that the ectopic beat correction operates to generate secondary timing data which typically differs from the primary timing data (cf. step 304 in FIG. 3), since the influence of ectopic beats is eliminated or at least reduced.

EBC Analysis (Calculation Procedure 606)

Ectopic beats may be analyzed in terms of how frequently they occur, solely requiring that their occurrence times are available. Their occurrence times are given by the classification data (which identifies the ecotopic heart pulses) in combination with the secondary timing data (which identifies the occurrence time of each heart pulse).

The EBC analysis may detect changes in the behavior of the occurrence times of the ectopic beats, i.e., changes in the intensity. Since the instantaneous intensity of the ectopic beats may be associated with a large variance, the mean intensity over a time window may be used as a parameter. The analysis is then performed by sliding the time window over the evaluation segment. If a fixed intensity is assumed within the time window, a blockwise updated trend describing the intensity of ectopic beats may be obtained.

The easiest way to measure the intensity of ectopic beats within a window would simply be to count the number of ectopic beats present within that window.

Another parameter that represents the intensity of ectopic beats may be obtained by modelling the occurrence times by a random point process, or a counting process which describes the number of ectopic beats until a given time (i.e., the integral of the point process). The counting process may be modelled by a least informative statistical distribution, namely, the Poisson process. Accordingly, the interval lengths between successive occurrence times will be independent of each other and completely characterized by an exponential probability density function (PDF) with an intensity parameter. The maximum likelihood estimate (MLE) of this intensity parameter may be derived, which will represent the intensity of the ectopic beats.

HRT Analysis (Calculation Procedure 608)

The short-term fluctuation in heart rate which follows a ventricular ectopic beat (VEB) is referred to as heart rate turbulence (HRT). In normal subjects, the heart rate first increases and then decreases to baseline, immediately after a VEB. The increase in heart rate is hypothesized to be due to compensation of the sudden drop in blood pressure induced by the VEB and subsequently sensed by the baroreceptors. Once blood pressure is restored, the heart rate returns to baseline in order to maintain the blood pressure. The subject's ability to recover from a local decrease in blood pressure is reflected by the strength of turbulence. The spectral content of HRT is typically in the LF band (0.04-0.15 Hz), since the LF band is affected by the baroreceptor reflex and a blood pressure peak often appears around 0.1 Hz. The absence of HRT reflects autonomic dysfunction. It has been demonstrated that HRT is a powerful predictor of mortality after acute myocardial infarction. The analysis of HRT offers considerable potential in other areas as well, e.g., congestive heart failure, diabetes mellitus, and hypotension in hemodialysis patients.

Figure 8:
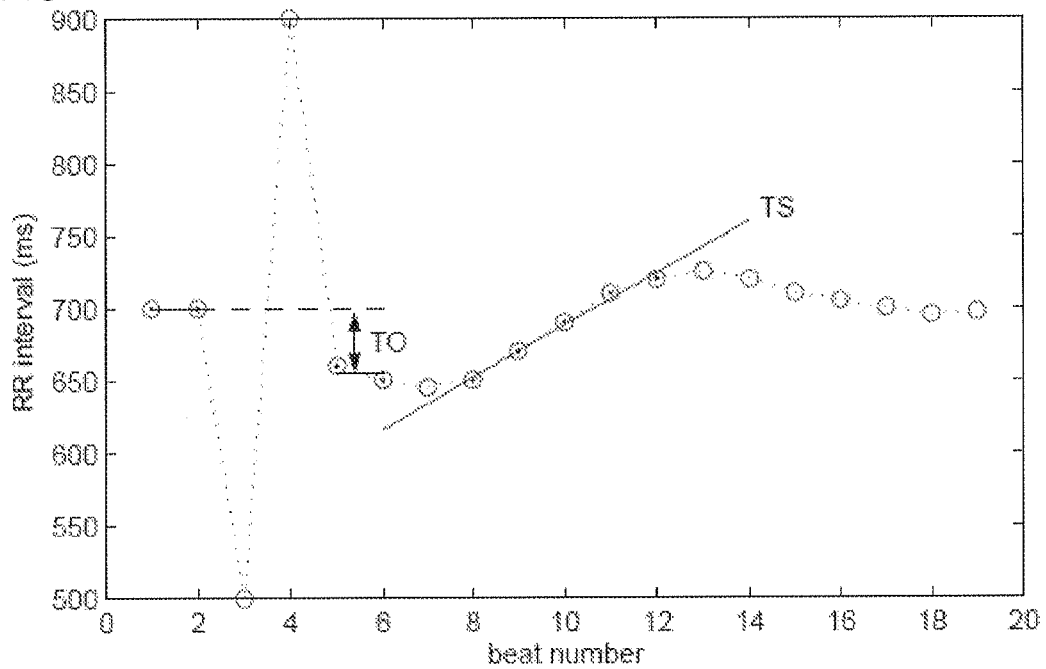
FIG. 8 is an RR interval tachogram that illustrates various parameters indicative of heart rate turbulence.

Several parameters for HRT characterization have been presented of which turbulence onset (TO) and turbulence slope (TS) are, by far, the most commonly employed. FIG. 8 is an RR interval tachogram for a normal subject, wherein beat numbers 3 and 4 are the shortened and prolonged RR intervals induced by a VEB (the coupling interval and the compensatory pause). In FIG. 8, the two HRT parameters TO and TS are also illustrated.

The parameter TO is a measure of the initial acceleration in heart rate and TS is a measure of the deceleration of heart rate back to baseline. The parameter TO is the relative change of RR intervals enclosing a VEB, defined by the relative difference of the averages of the two normal RR intervals before and after the VEB. Since TO measures the relative change in RR intervals, negative values of TO imply heart rate acceleration following the VEB, whereas positive values imply heart rate deceleration. The parameter TS is defined by the steepest slope observed over 5 consecutive RR intervals in the first 15 RR intervals following the VEB, see FIG. 8. Prior to computation of TO and TS, an average RR interval tachogram is determined from available VEBs. Several studies have shown that TS is clinically more powerful than TO, e.g., as a predictor of mortality after acute myocardial infarction. However, TS has certain drawbacks. First, TS is overestimated at low signal-to-noise ratios (SNRs), i.e., when few VEBs are used for averaging or when the underlying HRV is considerable. Second, TS leads to structural correlation between HRT and heart rate. A low heart rate produces large TS, and, conversely, a high heart rate produces small TS, due to the very definition of TS.

Besides TO and TS, several other HRT parameters have been presented of which the majority are closely related to TO and TS, such as combined TO and TS analysis, and an adjusted TS parameter with respect to either heart rate or the number of averaged beats. Furthermore, the first beat number of the 5 RR interval sequence from which TS is determined (i.e., where the steepest slope of RR intervals is observed) is denoted turbulence timing. The correlation coefficient of TS is defined as the correlation coefficient of the regression line fitted to the 5 RR intervals of TS. Other parameters are the turbulence jump, defined as the maximum difference between adjacent RR intervals, and the turbulence dynamics, quantifying the correlation between TS and heart rate. Yet another parameter is the turbulence frequency decrease that results from fitting a sine function to the RR intervals following the compensatory pause. The relationship between HRT and heart rate has been analyzed, where several studies have shown a correlation between them; low heart rate associated with large HRT, and high heart rate with small HRT. This correlation may be due to that the degree of blood pressure reduction induced by a VEB is influenced by heart rate. The relationship between HRT and heart rate has been suggested to have diagnostic value when quantified as turbulence dynamics, i.e., the steepness of the correlation; strong correlation is considered healthy.

Furthermore, a generalized likelihood ratio test (GLRT) statistic has been proposed for detection and characterization of heart rate turbulence (HRT), where a set of Karhunen-Loéve basis functions models HRT. The detector structure is based on an extended integral pulse frequency modulation (IPFM) model which accounts for the presence of ectopic beats and HRT. In one variant, the test statistic takes a priori information regarding HRT shape into account, whereas another variant uses a GLRT detector that relies solely on the energy contained in the signal subspace.

Heart Shape Analysis of Average Representation (Calculation Procedure 516)

As noted in relation to FIG. 5, the heart shape analysis may be performed on either an average representation of normal heart pulses or an average representation of ectopic heart pulses.

Average Representation of Normal Heart Pulses

The average shape of the normal heart pulses may, e.g., be used in order to determine arterial stiffness, and/or degree of calcification, and/or flow rate.

Arterial Stiffness:

The heart pulse waveform has two phases: the rising and falling edges of the pulse (the anacrotic and catacrotic phases). Systole is mainly associated with the first phase, while the second phase is associated with diastole and wave reflections from the periphery. Subjects with healthy compliant arteries usually have a dicrotic notch in the catacrotic phase. FIG. 9(a) is a plot of a normalized average heart pulse of a young healthy person, exhibiting a dicrotic notch. It has been shown in healthy subjects that the process of hardening/stiffening of the arteries may start from around the first or second decades of life, and may be accelerated by medical conditions including renal disease and diabetes mellitus. Arterial stiffness is associated with hypertension, a risk factor for stroke and heart disease. A common cause of death in renal patients is sudden cardiac death, where coronary artery disease is the predominant cause. Stiffening of the arteries cause the dicrotic notch and higher harmonic frequencies in the heart pulse signal to be diminished. Thus, vascular ageing causes a triangulation in the normalized heart pulse shape. This is illustrated in FIG. 9(b) which is a plot of a normalized average heart pulse of an old renal patient.

Clearly, parameter values may be calculated based on shape of the average heart pulse to represent the degree of arterial stiffness.

Calcification:

In dialysis patients calcification is a common co-morbidity. There is a high correlation between calcification and arterial stiffness, since calcification may cause arterial stiffness. Thus, parameter values representing arterial stiffness may also be used to represent the degree of calcification.

Stenosis:

There is a correlation between calcification/arterial stiffness and stenosis. Thus, parameter values representing arterial stiffness may also used to indicate an elevated risk for stenosis, e.g. in the blood vessel access.

Cardiovascularflow Rate:

Monitoring of cardiovascular flows may provide numerous benefits, in particular in connection with extracorporeal treatments. One cardiovascular flow is cardiac output, which is the quantity of blood pumped each minute by the heart into the aorta, i.e. the total blood flow in the circulation of the subject. Monitoring of cardiac output may e.g. be beneficial in connection with dialysis since water removal, i.e. ultrafiltration, during dialysis may reduce cardiac output, which may lead to an increased risk for the subject undergoing the treatment to suffer from hypotension. The reason is that cardiac output depends on the venous blood flow returning to the heart, which in turn may decrease as the total blood volume decreases (relative blood volume reduction) after running ultrafiltration at higher rate compared to the vascular refill rate.

Continuous or intermittent measurement of cardiac output may be important in adjusting the ultrafiltration rate properly to reduce the risk for hypotension. In addition, variation in cardiac output between treatments or over longer periods may be an indication of a heart condition, which may call for further medical investigation. Additionally, provided that other properties of the cardiovascular system remain constant over time, e.g. no stenosis formation, a calibration of the cardiac output measurement may remain valid and be used for monitoring of long-term changes in cardiac output.

Another cardiovascular flow is access flow, which is the flow of blood that passes the blood vessel access. Access flow measurement may be important for the clinician to determine if a blood vessel access of a dialysis patient is capable of providing sufficient blood flow to allow adequate dialysis treatment. Normally, access flow measurements are conducted regularly, e.g. once a month, using specialized equipment, in order to detect low values or declining trends. Such indications may urge the physician to perform an access intervention by angioplasty or surgery to alleviate the situation.

The present Assignee has found that pressure variations in the extracorporeal circuit may be caused by pressure and flow variations in the cardiovascular system. Thus, variations in e.g. cardiac output and access flow both cause variations in the heart pulses in the evaluation segment, e.g. manifested as variations in amplitude, shape and phase. Hence, by monitoring pressure variations in the extracorporeal circuit and relating these variations to relevant cardiovascular relationships, a parameter value representing a particular cardiovascular flow rate may be determined. These variations may be monitored for individual normal heart pulses in the evaluation segment, but may also be identified in the average representation.

For example, it has been found that the cardiovascular flow rate selectively affects the damping and delay of the frequency components of the heart pulses, and thereby the shape of the normal heart pulses. Thus, a parameter value indicative of the cardiovascular flow rate may be obtained by mapping the average representation of the normal heart pulses against a set of predetermined heart signal profiles, each representing a particular cardiovascular flow rate. Alternatively, the parameter value may be derived from the magnitude (e.g. maximum amplitude) of the average representation, since the magnitude may be proportional to the cardiovascular flow rate.

In addition to the above description, reference is also made to U.S. provisional application No. 61/290,319, entitled "Device and method for monitoring a fluid flow rate in a cardiovascular system", which was filed on 28 Dec. 2009 and which is incorporated herein in its entirety by this reference.

Average Representation of Ectopic Heart Pulses

The average shape of the ectopic heart pulses may, e.g., be used in order to determine the origin of the ectopic beat, and/or arterial stiffness, and/or degree of calcification, and/or flow rate.

Origin of Ectopic Beat:

The shape of the averaged ectopic pulse may be used to identify the origin of the ectopic beat, since the shape of the ectopic pulse is known to vary considerably depending on the source of the ectopy. There is generally a greater similarity in shape between a supraventricular ectopic pulse (an ectopic pulse which originates from the atria) and a normal heart pulse, than between a ventricular ectopic pulse (an ectopic pulse which originates from the ventricle) and a normal heart pulse. Furthermore, the shape of different ventricular ectopic pulses may also vary depending on where in the ventricle the ectopic beat is initiated. The origin of the ectopic pulse may be determined according to the above-described classification techniques based on shape data. From a medical point of view it may be important to know the origin of the ectopic beat. Depending on the origin, different decisions (e.g., medication, surgery, follow-up, continue with additional testing) may be taken in order to assure patient well-being.

Arterial Stiffness:

Like for normal heart pulses, the shape of the averaged ectopic heart pulse may change depending on the stiffness of the arteries. The change in shape is similar to that of the average normal heart pulses, i.e., the higher harmonic frequencies in the ectopic heart pulse signal may be diminished with increasing arterial stiffness.

Calcification:

There is a high correlation between calcification and arterial stiffness, since calcification may cause arterial stiffness. Thus, parameter values representing arterial stiffness may also used to represent the degree of calcification.

Stenosis:

There is a correlation between calcification/arterial stiffness and stenosis. Thus, parameter values representing arterial stiffness may also used to indicate an elevated risk for stenosis, e.g. in the blood vessel access.

Cardiovascular Flow Rate:

Like for normal heart pulses, the amplitude, shape and phase of the ectopic heart pulses may change depending on the flow rate. Thus, these cardiovascular properties may be assessed based on the average representation of ectopic heart pulses in the same way as for normal heart pulses, although possibly based on different criteria.

III. Signal Processing of Pressure Signal

This Section describes different techniques for removing/suppressing pump pulses in a pressure signal obtained by sampling measurement data from a pressure wave sensor in an apparatus such as the dialysis machine in FIG. 1. Still further, as explained above, more than one physiological phenomenon in the patient may give rise to pressure pulses in the pressure signal. Such physiological phenomena include the breathing system, the autonomous system for blood pressure regulation and the autonomous system for body temperature regulation. In certain situations, it may thus be desirable to process the pressure signal for isolation of heart pulses among other physiological pulses.

Figure 10:
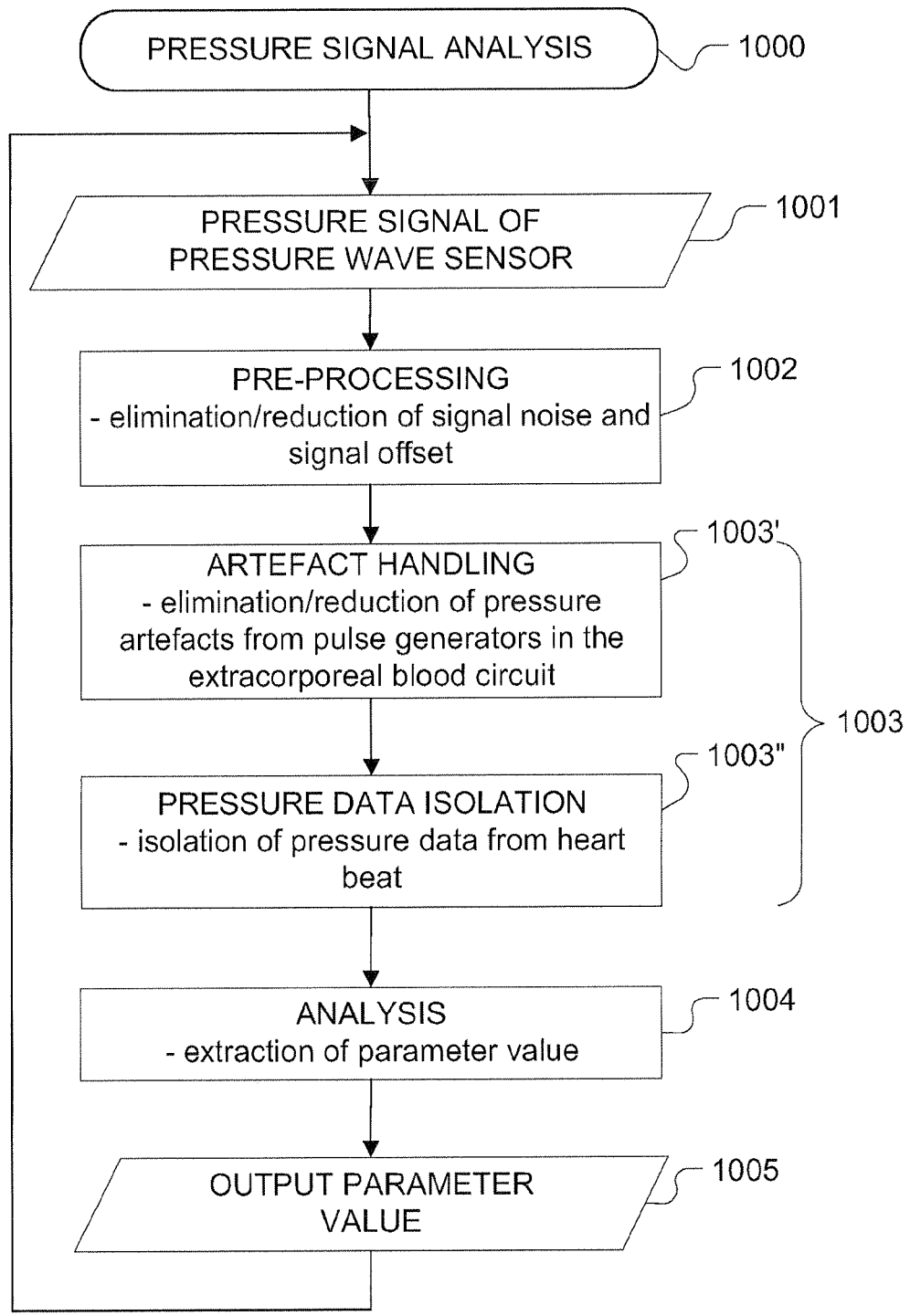
FIG. 10 is a flow chart of a process for signal analysis of a pressure signal obtained in the system configuration of FIG. 1.

FIG. 10 is a flow chart that illustrates steps of a signal analysis process 1000 according to an embodiment of the present invention. It is initiated by acquiring a pressure signal, step 1001, e.g. from the venous or the arterial pressure sensor (4a, 4c in FIG. 1), comprising a number of pressure wave-induced signal components. The signal analysis process may be divided into a number of main steps: a pre-processing step 1002, a signal extraction step 1003 and an analysis step 1004. The pre-processing step 1002 includes elimination or reduction of signal noise, such as offset, high frequency noise and supply voltage disturbances. The signal extraction step 1003 may conceptually be separated into two sub-steps: an elimination or reduction of pressure artefacts (pump pulses) originating from pulse generators in (or associated with) the extracorporeal fluid system (step 1003') and an isolation of pressure data originating from heartbeats (step 1003"). In the context of the present disclosure, the signal extraction step 1003 denotes a process of generating a time-dependent signal (also denoted "monitoring signal" herein) which is free or substantially free from any unwanted pressure modulations.

It should be noted that the steps 1002, 1003', 1003" may be executed in any order, and also that the functionality of one step may be included in another step. For example, all or part of the elimination of signal noise and signal offset (i.e. step 1002), as well as all or part of the elimination of pressure artefacts (step 1003'), may be included in the algorithms for pressure data isolation (step 1003"). For instance, the pressure signal may be band-pass filtered or low-pass filtered to isolate the heart pulses in a way such that signal noise and/or signal offset and/or pressure artefacts are eliminated from the pressure signal. Furthermore, any of steps 1002, 1003' and 1003" may be omitted, depending on the amount of signal interference and the required quality of the resulting monitoring signal.

In the analysis step 1004, a dedicated signal analysis algorithm is applied for extraction of a parameter value, e.g. as described in Section II above. Thus, step 1004 may correspond to steps 302-310 in FIG. 3. In step 1005, which corresponds to step 312 in FIG. 3, the parameter value is output.

In the following, different embodiments of the signal extraction step 1003 will be exemplified and described in further detail.

Elimination of Artefacts (Step 1003')

In the simplest case, no pump or other source of pressure artefacts is present in the extracorporeal circuit 20 (FIG. 1) connected to the patient during the data acquisition. For instance, the blood pump 3 may have been shut down. In such a case, step 1003' may be omitted.

In the general case, however, one or more pumps are running or other sources of cyclic or non-cyclic, repetitive or non-repetitive artefacts are present during the data acquisition. Information on cyclic disturbances may be known from external sources, e.g. other sensors (e.g. the pump sensor 26 in FIG. 1), or may be estimated or reconstructed from system parameters.

Cyclic pressure artefacts may originate from operating one or more blood pumps, and further pumps such as pumps for dialysis fluid, repetitive actuation of valves, and movements of membranes in balancing chambers. According to the findings in connection with the present invention, artefacts may also originate from mechanical resonance of system components such as swinging movements of bloodlines energized by e.g. a pump. Frequencies of bloodline movements are given by the tube lengths and harmonics thereof and by the beating between any frequencies involved, i.e. between different self-oscillations and pump frequencies. These frequencies may differ between the venous and arterial lines. Mechanical fixation of the bloodlines and other free components may remedy the problem of mechanical resonance. Alternatively, an operator may be instructed to touch or jolt the blood lines to identify natural frequencies associated with the blood lines, which information may be used in the analysis for improved removal of components not belonging to the pressure data of interest.

Examples of non-cyclic artefacts are subject movement, valve actuation, movements of tubing, etc.

Elimination of artefacts may, e.g., be provided by:
Controlling a pulse generator in the extracorporeal fluid system, such as a pump
By temporarily shutting down the pulse generator;
Shifting the pulse generator frequency;
Low pass, band pass or high pass filtering;
Spectral analysis and filtering in the frequency domain;
Time domain filtering.

Controlling a Pulse Generator

Artefacts from a pulse generator, such as a pump, in the extracorporeal circuit may be avoided by temporarily shutting down (disabling) the pulse generator, or by shifting the frequency of the pulse generator away from the frequencies of the heartbeats.

A feedback control with respect to the heart rate, e.g. obtained from a dedicated pulse sensor attached to the patient or obtained via the HR analysis in one or more preceding iterations of the heart pulse analysis (cf. FIG. 3 in combination with calculation procedure 508 in FIG. 5 or calculation procedure 604 in FIG. 6), may be used to set the pump frequency optimally for detection of heart pulses. Hence, the control unit 23 of FIG. 1 may be operated to control the pump frequency in order to facilitate the detection of the heart pulses, e.g. the pump frequency may be controlled to minimize any overlap in frequency between the pump pulses and the heart pulses. For example, the pump frequency may be periodically increased and decreased around the overlap frequency, so as to maintain the overall blood flow rate. In a variant, the pump frequency is instead controlled so as to synchronize the rate of pump pulses with the rate of heart pulses while applying a phase difference between the pump pulses and the heart pulses. Thereby, the pump pulses and the heart pulses will be separated in time, and the heart pulses may be detected in the time domain, even without removal of the pump pulses. The phase difference may be approximately 180°, since this may maximize the separation of the pump pulses and the heart pulses in the time domain. This so-called phase-locking technique may be activated when it is detected that the rate of heart pulses approaches the rate of pump pulses, or vice versa.

In one embodiment, the surveillance device 25 operates as master and is thus able to instruct the control unit 23 to shift frequency of the blood pump 3 or temporarily shut down the blood pump 3. In another embodiment, the control of the blood pump 3 is executed independently of the surveillance device 25, e.g. by the control unit 23 or another controller in the dialysis machine, which triggers the surveillance device 25 to execute the signal analysis process 1000 on the pressure signal when the blood pump 3 has been appropriately controlled.

Applying Low Pass, Band Pass or High Pass Filters

The input signal to step 1003' may be fed into a filter, e.g. digital or analog, with frequency characteristics, such as frequency range and/or centre of frequency range, matched to the frequencies generated by a pulse generator, such as the blood pump 3 (FIG. 1), in the extracorporeal circuit. For instance, in a case where the blood pump operates within the frequency range of 1 Hz, a suitable low pass filter may be applied in order to remove pressure artefacts above 1 Hz while retaining frequency components of the heart pulses below 1 Hz. Correspondingly, a high pass filter may be applied to retain frequency components of the heart pulses above a frequency of the pulse generator. Alternatively, one or more notch filters or the like may be utilised to remove/attenuate frequencies in one or more confined ranges.

Spectral Analysis and Filtering in the Frequency Domain

The input signal to step 1003' may be subjected to spectral analysis, e.g. by applying a Fourier transformation technique, such as FFT (Fast Fourier Transform) to convert the input signal into the frequency domain. The resulting energy spectrum (amplitude spectrum) may then be multiplied by an appropriate filter function and then re-transformed into the time domain. There are many alternative and equivalent filtering techniques available to the skilled person.

Time Domain Filtering

Artefact elimination by filtering in the time domain is further disclosed and exemplified below in Sections IV and V. In addition to Sections IV and V, reference is also made to WO2009/156175, which is incorporated herein in its entirety by this reference.

By filtering the pressure signal in the time domain, it is possible to essentially eliminate artefacts, even if the artefacts and heart pulses overlap or nearly overlap in the frequency domain, and even if the heart pulses are much smaller in amplitude than the artefacts. By "essentially eliminating" is meant that the artefacts are removed from the pressure signal to such an extent that the heart pulses can be detected and analysed for the purpose of monitoring a cardiovascular property of the patient.

A frequency overlap is not unlikely, e.g. if one or both of the artefacts and the heart pulses is made up of a combination of frequencies or frequency ranges.

Furthermore, the frequency, amplitude and phase content of the artefacts and the heart pulses may vary over time. For example, such variations are known occur in the heart rhythm, as explained in Section II above.

Any frequency overlap may make it impossible or at least difficult to remove artefacts by conventional filtering in the frequency domain. Furthermore, frequency variations may make it even harder to successfully remove artefacts, since the frequency overlap may vary over time. Even in the absence of any frequency overlap, frequency variations may make it difficult to define filters in the frequency domain.

Still further, the time domain filtering may make it possible to remove artefacts for individual heart pulses, and may thus improve the response time compared to filtering in the frequency domain, which may need to operate on a sequence of artefacts and heart pulses in the pressure signal.

Isolating Pressure Data from a Heart Beat (Step 1003")

Isolating pressure data originating from one or more heart beats may be provided by any or a combination of:
 Low pass, band pass or high pass filtering;
 Spectral analysis and filtering in the frequency domain; or
 Time domain filtering.

Applying Low Pass, Band Pass or High Pass Filters

The input signal to step 1003" may be fed into a filter, e.g. digital or analog, with frequency characteristics, such as frequency range and/or centre of frequency range, matched to the frequencies of the heart pulses. Typically such filtering may pass frequencies in the range of about 0.5-3 Hz.

According to an alternative, the surveillance device 25 is configured to set the cut-off frequency or frequencies of the filter, at least in part, based on patient-specific information, i.e. existing data records for the patient, e.g. obtained in earlier treatments of the same patient. The patient-specific information may be stored in an internal memory of the surveillance device 25, on an external memory which is made accessible to the surveillance device, or on a patient card where the information is e.g. transmitted wirelessly to the surveillance device, e.g. by RFID (Radio Frequency IDentification).

Spectral Analysis and Filtering in the Frequency Domain

The input signal may be subjected to spectral analysis, e.g. by applying a Fourier transformation technique, such as FFT (Fast Fourier Transform) to convert the input signal into the frequency domain. The resulting energy spectrum (amplitude spectrum) may then be multiplied by an appropriate filter function and then re-transformed into the time domain. There are many alternative and equivalent filtering techniques available to the skilled person.

Time Domain Filtering

Pressure data originating from heartbeats may be extracted as an error signal of an adaptive filter. The adaptive filter is fed with both the input signal and a predicted signal profile of a cyclic disturbance. The cyclic disturbance may be one or more pressure pulses from any other physiological phenomenon (e.g. breathing). Particularly, a reconstructed pressure profile originating from the breathing system of the patient may be input to the adaptive filter. This and other time domain filtering techniques for removing unwanted signal components from a measurement signal is further disclosed and exemplified in Section V below. Although Section V is concerned with eliminating pressure artefacts originating from a pulse generator in an extracorporeal circuit, such as a pumping device, it is equally applicable for eliminating e.g. pulses originating from unwanted physiological phenomena, as long as a predicted signal profile of the unwanted pulses may be obtained. The skilled person realizes that such a predicted signal profile may be obtained in ways equivalent to those described in Section IV below. Such ways include using a signal profile which is fixed and predetermined, e.g. by simulation or reference measurement, using a signal profile which is intermittently updated based on reference measurements, using a signal profile which is obtained from a reference library based on one or more current system parameter values, and using a signal profile which is obtained by modifying a predetermined profile based on one or more current system parameter values. The system parameter values may relate to a rate of heart/breathing pulses.

IV. Obtaining a Pump Profile

This Section describes different embodiments for predicting or estimating the signal profile of pump pulses in any one of the system configurations discussed herein. The predicted signal profile is typically given as a series of pressure values over a period of time normally corresponding to at least one complete pump cycle (pump stroke) of the blood pump 3.

Figure 11:
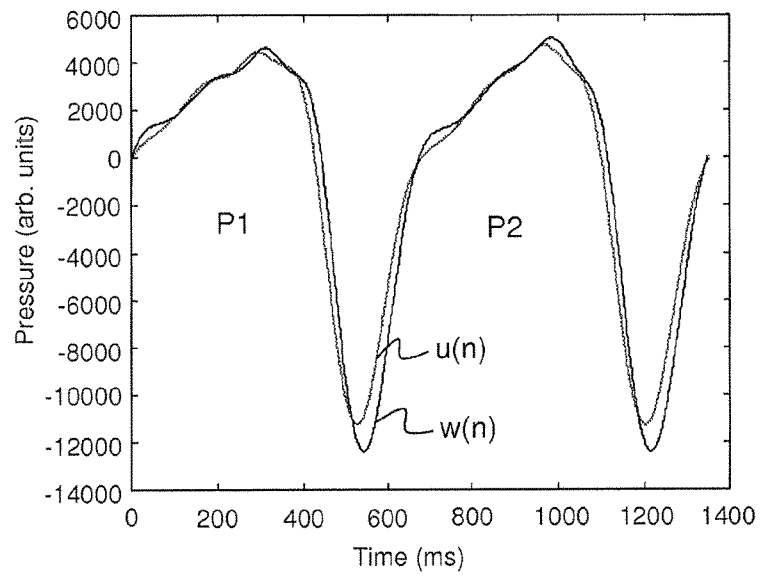
FIG. 11 is a plot of a reference profile of pump pulses in a pressure signal acquired from a venous pressure sensor in the system of FIG. 1.

FIG. 11 illustrates an example of a predicted signal profile u(n) for the system in FIG. 1, and specifically for the pressure signal obtained from the venous pressure sensor 4c. Since the blood pump 3 is a peristaltic pump, in which two rollers 3a, 3b engage a tube segment during a full revolution of the rotor 3', the pressure profile consists of two pump strokes. The pump strokes may result in different pressure values (pressure profiles P1, P2), e.g. due to slight differences in the engagement between the rollers 3a, 3b and the tube segment, and thus it may be desirable for the predicted signal profile to represent both pump strokes. If a lower accuracy of the predicted signal profile may be tolerated, e.g. if the output of the subsequent removal process (see Section V) is acceptable, the predicted signal profile might represent one pump stroke only.

On a general level, the predicted signal profile may be obtained in a reference measurement, through mathematical simulation of the fluid system, or combinations thereof.

Reference Measurement

A first main group of methods for obtaining the predicted signal profile is based on deriving a time-dependent reference pressure signal ("reference signal") from a pressure wave sensor in the system, typically (but not necessarily) from the same pressure wave sensor that provides the measurement signal (pressure signal) that is to be processed for removal of pump pulses. During this reference measurement, the heart pulses are prevented from reaching the relevant pressure wave sensor, by isolating the pressure wave sensor from the pulse waves generated by the heartbeats. For example, the reference measurement may be carried out during a priming phase, in which the extracorporeal circuit 20 is detached from the patient and a priming fluid is pumped through the bloodlines. Alternatively, the reference measurement may be carried out in a simulated treatment with blood or any other fluid. Optionally, the reference measurement may involve averaging a plurality of pump pulses to reduce noise. For example, a plurality of relevant signal segments may be identified in the reference signal, whereupon these segments are aligned to achieve a proper overlap of the pump pulses in the different segments and then added together. The identifying of relevant signal segments may be at least partially based on timing information ("pump pulse timing") which indicates the expected position of each pump pulse in the reference signal. The pump pulse timing may be obtained from a trigger point in the output signal of the pump sensor 26, in a control signal of the control unit 23, or in the pressure signal from another one of the pressure sensors 4a-4c. For example, a predicted time point of a pump pulse in the reference signal may be calculated based on a known time delay between the trigger point and the pressure sensor that generates the reference signal. In variant, if the pump pulses are periodic, relevant signal segments may be identified by identifying crossing points between the reference signal and a given signal level, wherein the relevant signal segments are identified to extend between any respective pairs of crossing points.

In a first embodiment, the predicted signal profile is directly obtained in a reference measurement before the extracorporeal circuit 20 is connected to the patient, and is then used as input to the subsequent removal process, which is executed during the monitoring process (e.g. the heart pulse analysis in FIG. 3). In this embodiment, it is thus assumed that the predicted signal profile is representative of the pump pulses when the extracorporeal circuit 20 is connected to the patient. Suitably, the same pump frequency/speed is used during the reference measurement and during the monitoring process. It is also desirable that other relevant system parameters are maintained essentially constant.

Figure 12:
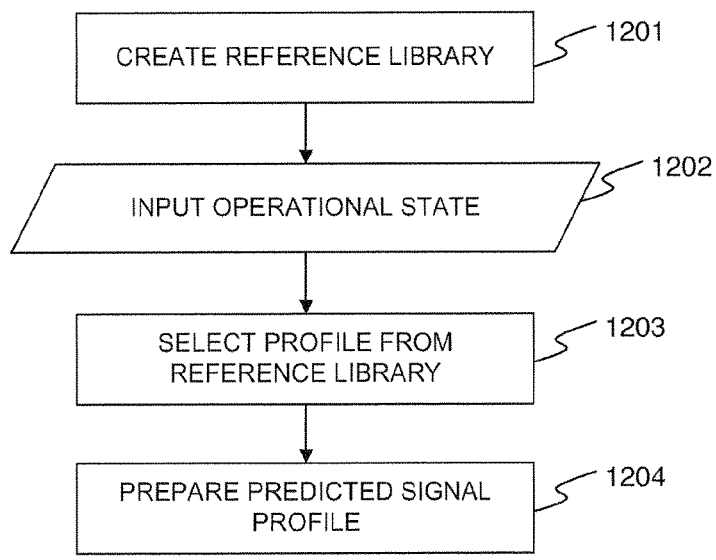
FIG. 12 is a flow chart of a process for obtaining a predicted signal profile.

FIG. 12 is a flow chart of a second embodiment. In the second embodiment, a reference library or database is first created based on the reference measurement (step 1201). The resulting reference library is typically stored in a memory unit, e.g. RAM, ROM, EPROM, HDD, Flash, etc (cf. DB in FIG. 4) in the surveillance device 25. During the reference measurement, reference pressure signals are acquired for a number of different operational states of the extracorporeal circuit. Each operational state is represented by a unique combination of system parameter values. For each operational state, a reference profile is generated to represent the signal profile of the pump pulses. The reference profiles together with associated system parameter values are then stored in the reference library, which is implemented as a searchable data structure, such as a list, look-up table, search tree, etc.

During the actual monitoring process, i.e. when pump pulses are to be eliminated from the pressure signal, current state information indicating the current operational state of the extracorporeal circuit 20 is obtained from the system, e.g. from the pump sensor 26, the control unit 23 or otherwise (step 1202). The current state information may include a current value of one or more system parameters. The current value is then matched against the system parameter values in the reference library. Based on the matching, one or more reference profiles are selected (step 1203) and used for preparing the predicted signal profile (step 1204).

Generally, the aforesaid system parameters represent the overall system state, including but not limited to the structure, settings, status and variables of the dialysis machine or its components. In the system of FIG. 1, exemplary system parameters may include:

Pump-related parameters: number of active pumps connected directly or indirectly (e.g. in a fluid preparation system for the dialyser) to the extracorporeal circuit, type of pumps used (roller pump, membrane pump, etc), flow rate, revolution speed of pumps, shaft position of pump actuator (e.g. angular or linear position), etc Dialysis machine settings: temperature, ultrafiltration rate, mode changes, valve position/changes, etc Disposable dialysis equipment/material: information on pump chamber/pump segment (material, geometry and wear status), type of bloodline (material and geometry), type of dialyser, type and geometry of access devices, etc Dialysis system variables: actual absolute pressures of the system upstream and downstream of the blood pump, e.g. venous pressure (from sensor 4c), arterial pressure (from sensor 4a) and system pressure (from sensor 4b), gas volumes trapped in the flow path, blood line suspension, fluid type (e.g. blood or dialysis fluid), etc Patient status: blood access properties, blood properties such as e.g. hematocrit, plasma protein concentration, etc It is to be understood that any number or combination of system parameters may be stored in the reference library and/or used as search variables in the reference library during the monitoring process.

In the following, the second embodiment will be further explained in relation to a number of examples. In all of these examples, the pump revolution frequency ("pump frequency"), or a related parameter (e.g. blood flow rate) is used to indicate the current operational state of the extracorporeal circuit 20 during the monitoring process. In other words, the pump frequency is used as search variable in the reference library. The pump frequency may e.g. be given by a set value for the blood flow rate output from the control unit 23, or by an output signal of the pump sensor 26. Alternatively, the pump frequency may be obtained by frequency analysis of the pressure signal from any of the sensors 4a-4c (FIG. 1) during operation of the fluid system. Such frequency analysis may be achieved by applying any form of harmonics analysis to the pressure signal, such as Fourier or wavelet analysis. As indicated in FIG. 2(b), the base frequency $f_0$ of the pump may be identified in a resulting power spectrum.

In the following, three examples are given of techniques for generating the predicted signal profile by accessing such a reference library.

Figure 13:
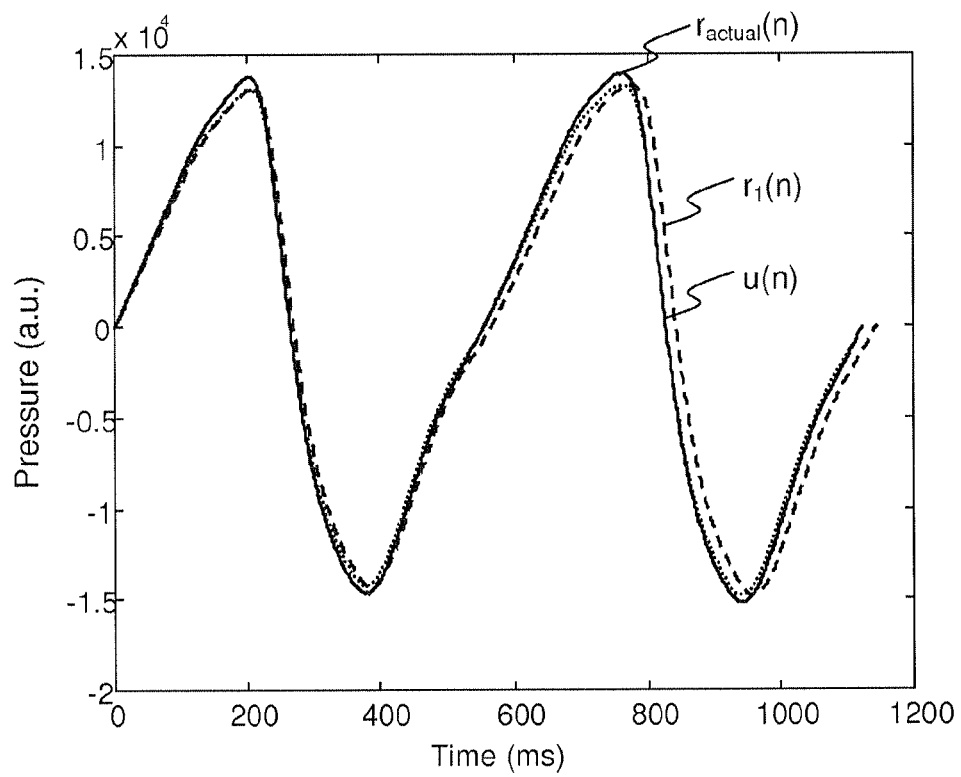
FIG. 13 is a plot to illustrate an extrapolation process for generating a predicted signal profile.

In a first example, the reference profiles stored in the reference library are temporal profiles. The reference library is searched for retrieval of the reference profile that is associated with the pump frequency that lies closest to the current pump frequency. If no exact match is found to the current pump frequency, an extrapolation process is executed to generate the predicted signal profile. In the extrapolation process, the retrieved reference profile is scaled in time to the current pump cycle, based on the known difference ("pump frequency difference") between the current pump frequency and the pump frequency associated with the retrieved reference profile. The amplitude scale may also be adjusted to compensate for amplitude changes due to pump frequency, e.g. based on a known function of amplitude as a function of pump frequency. FIG. 13 illustrates a reference profile $r_1(n)$ obtained at a flow rate of 470 ml/min, and a predicted signal profile u(n) which is obtained by scaling the reference profile to a flow rate of 480 ml/min. For comparison only, a reference profile $r_{actual}(n)$ obtained at 480 ml/min is also shown, to illustrate that extrapolation process indeed may yield a properly predicted signal profile.

In a second example, the reference profiles stored in the reference library are temporal profiles. The reference library is again searched based on current pump frequency. If no exact match is found to the current pump frequency, a combination process is executed to generate the predicted signal profile. Here, the reference profiles associated with the two closest matching pump frequencies are retrieved and combined. The combination may be done by re-scaling the pump cycle time of the retrieved reference profiles to the current pump frequency and by calculating the predicted signal profile via interpolation of the re-scaled reference profiles. For example, the predicted signal profile u(n) at the current pump frequency v may be given by:

$$u(n)=g(v-v_i)\cdot r_i(n)+(1-g(v-v_i))\cdot r_j(n),$$

wherein $r_i(n)$ and $r_j(n)$ denotes the two retrieved reference profiles, obtained at a pump frequency $v_i$ and $v_j$, respectively, after re-scaling to the current pump frequency v, and g is a relaxation parameter which is given as a function of the frequency difference $(v-v_i)$, wherein $v_i \leq v \leq v_j$ and $0 \leq g \leq 1$. The skilled person realizes that the predicted signal profile u(n) may be generated by combining more than two reference profiles.

Figure 14A:
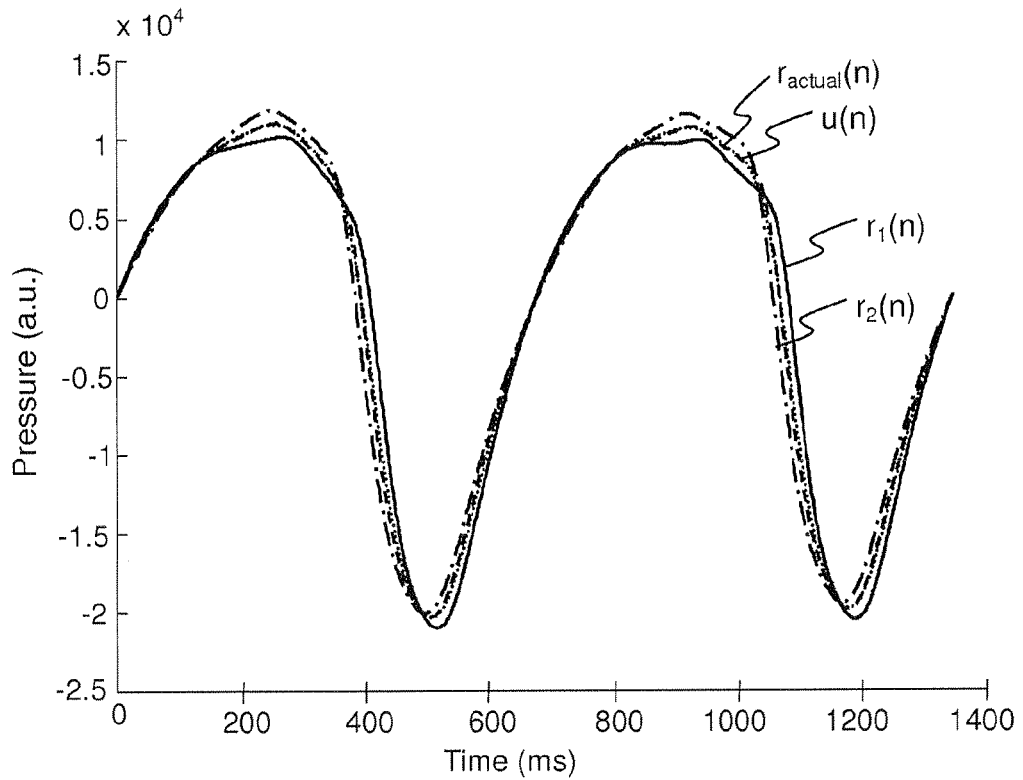
FIG. 14(a) is a plot to illustrate an interpolation process for generating a predicted signal profile.
Figure 14B:
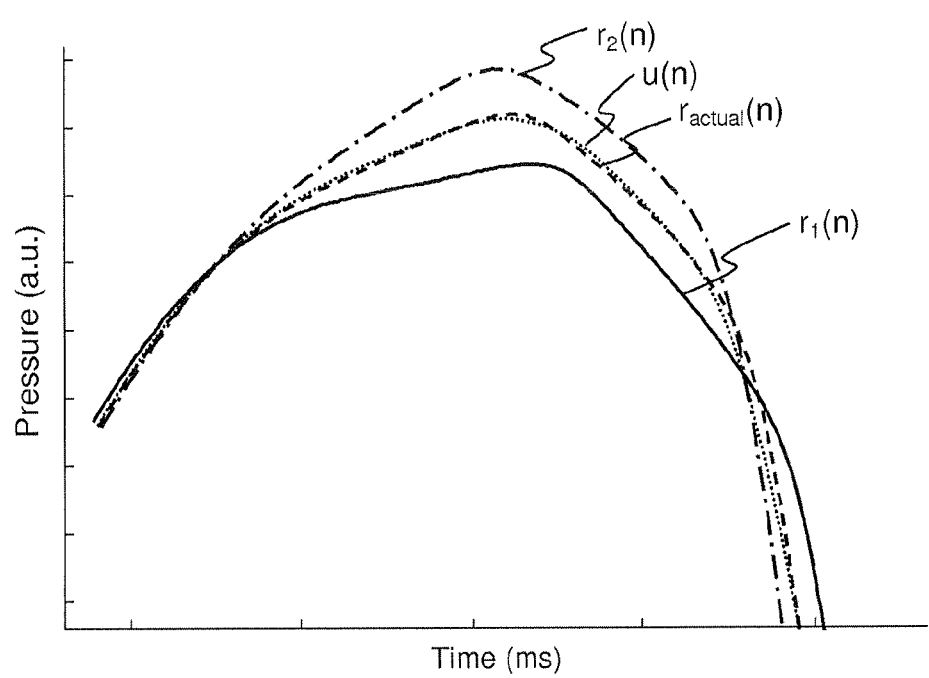
FIG. 14(b) is an enlarged view of FIG. 14(a).

FIG. 14(a) illustrates a predicted signal profile u(n) at a current flow rate of 320 ml/min for a pressure signal obtained from the venous sensor 4c in the system of FIG. 1. The predicted signal profile u(n) has been calculated as an average of a reference profile $r_1(n)$ obtained at a flow rate of 300 ml/min from the venous sensor and a reference profile $r_2(n)$ obtained at a flow rate of 340 ml/min from the venous sensor. For comparison only, a reference profile $r_{actual}(n)$ obtained at 320 ml/min is also shown, to illustrate that the combination process indeed may yield a properly predicted signal profile. In fact, the differences are so small that they are only barely visible in the enlarged view of FIG. 14(b).

The first and second examples may be combined, e.g. by executing the extrapolation process of the first example if the pump frequency difference is less than a certain limit, and otherwise executing the combination process of the second example.

In a third embodiment, like in the second embodiment shown in FIG. 12, a number of reference signals are acquired in the reference measurement, wherein each reference signal is obtained for a specific combination of system parameter values. The reference signals are then processed for generation of reference spectra, which are indicative of the energy and phase angle as function of frequency. These reference spectra may e.g. be obtained by Fourier analysis, or equivalent, of the reference signals. Corresponding energy and phase data are then stored in a reference library together with the associated system parameter values (cf. step 1201 in FIG. 12). The implementation of the reference library may be the same as in the second embodiment.

During the actual monitoring process, i.e. when pump pulses are to be eliminated from the pressure signal, a current value of one or more system parameters is obtained from the extracorporeal circuit (cf. step 1202 in FIG. 12). The current value is then matched against the system parameter values in the reference library. Based on the matching, a specific set of energy and phase data may be retrieved from the reference library to be used for generating the predicted signal profile (cf. step 1203 in FIG. 12). The predicted signal profile may be temporal and may be generated by adding sinusoids of appropriate frequency, amplitude and phase, according to the retrieved energy and phase data (cf. step 1204 in FIG. 12).

Generally speaking, without limiting the present disclosure, it may be advantageous to generate the predicted signal profile from energy and phase data when the pump pulses (to be removed) contain only one or a few base frequencies (and harmonics thereof), since the predicted signal profile may be represented by a small data set (containing energy and phase data for the base frequencies and the harmonics). One the other hand, when the power spectrum of the pump pulses is more complex, e.g. a mixture of many base frequencies, it may instead be preferable to generate the predicted signal profile from one or more temporal reference profiles.

Figure 15A:
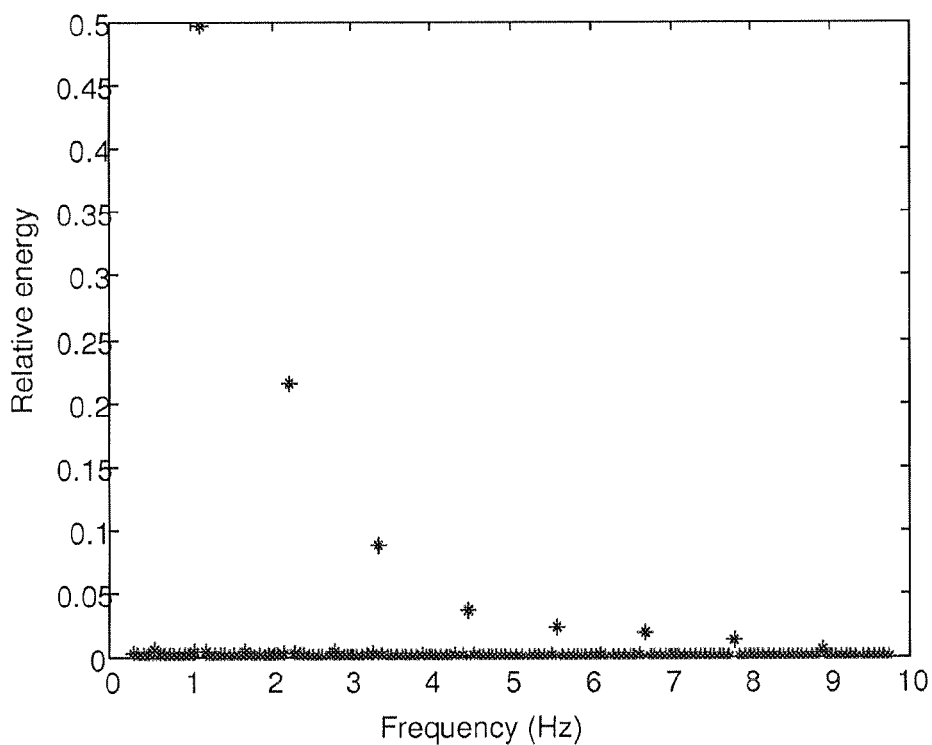
FIG. 15(a) represents a frequency spectrum of pump pulses at one flow rate.
Figure 15B:
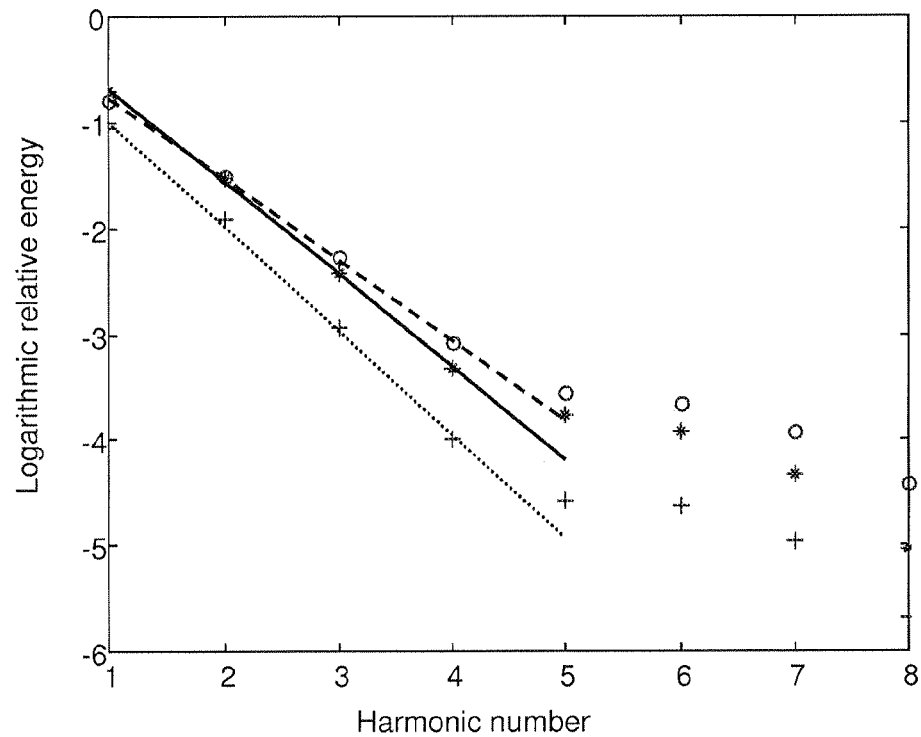
FIG. 15(b) represents corresponding frequency spectra for three different flow rates, wherein each frequency spectrum is given in logarithmic scale and mapped to harmonic numbers.
Figure 15C:
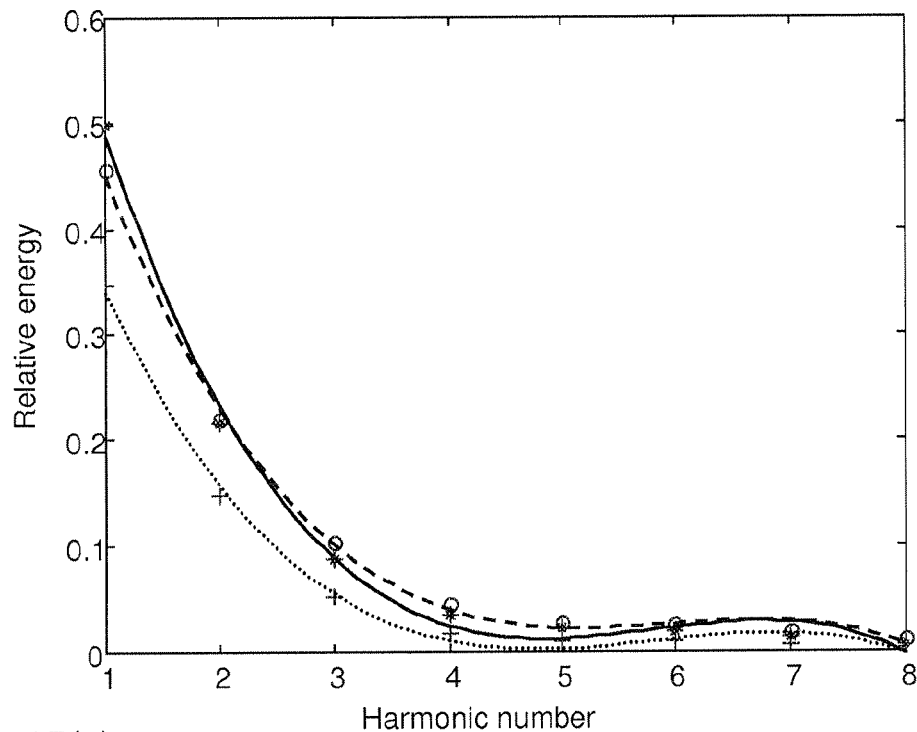
FIG. 15(c) is a plot of the data in FIG. 15(b) in linear scale.

FIG. 15(a) represents an energy spectrum of a reference signal acquired at a flow rate of 300 ml/min in the system of FIG. 1. In this example, the reference signal essentially consists of a basic pump frequency at 1.2 Hz ($f_0$, first harmonic) and a set of overtones of this frequency (second and further harmonics). Compared to the power spectrum of FIG. 2(b), the pressure signals used for generating the graphs in FIG. 15(a)-15(d) do not contain any significant frequency component at $0.5f_0$ and its harmonics. The graph in FIG. 15(a) displays the relative energy distribution, wherein the energy values have been normalized to the total energy for frequencies in the range of 0-10 Hz. FIG. 15(b) represents energy spectra of reference signals acquired at three different flow rates in the system of FIG. 1. The energy spectra are given in logarithmic scale versus harmonic number (first, second, etc). As shown, an approximate linear relationship may be identified between the logarithmic energy and harmonic number for the first four to five harmonic numbers. This indicates that each energy spectrum may be represented by a respective exponential/polynomial function. FIG. 15(c) illustrates the data of FIG. 15(b) in linear scale, wherein a respective polynomial function has been fitted to the data. As indicated in FIGS. 15(a)-15(c), the energy spectra may be represented in different formats in the reference library, e.g. as a set of energy values associated with discrete frequency values or harmonic numbers, or as an energy function representing energy versus frequency/harmonic number.

Figure 15D:
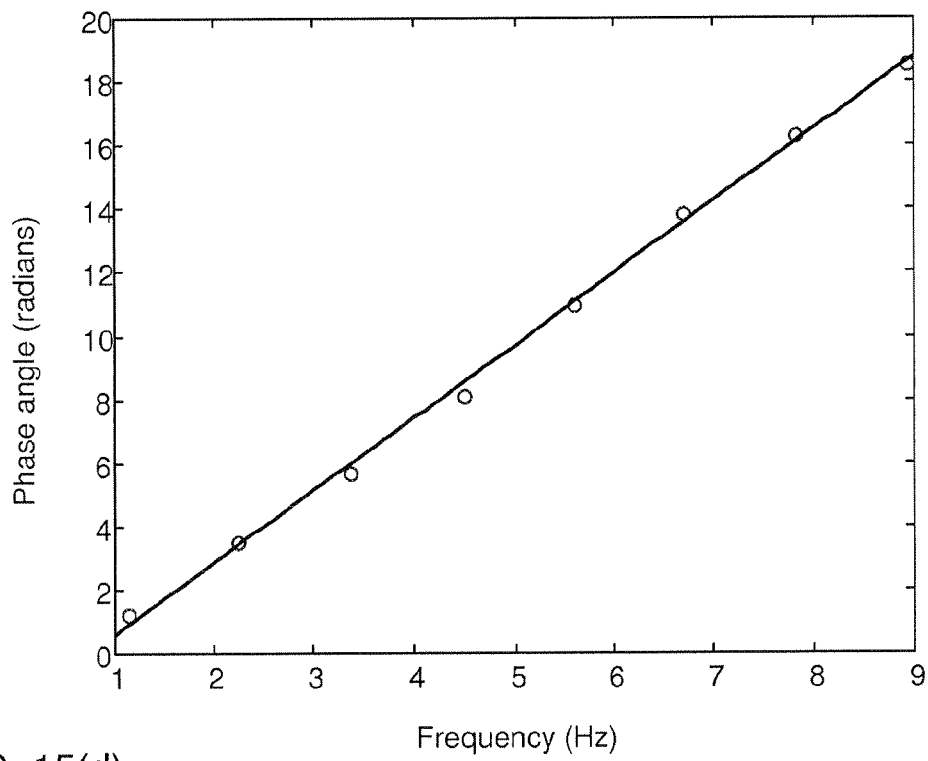
FIG. 15(d) is a phase angle spectrum corresponding to the frequency spectrum in FIG. 15(a).

FIG. 15(d) illustrates a phase angle spectrum acquired together with the energy spectrum in FIG. 15(a), i.e. for a flow rate of 300 ml/min. The graph in FIG. 15(d) illustrates phase angle as a function of frequency, and a linear function has been fitted to the data. In an alternative representation (not shown), the phase spectrum may be given as a function of harmonic number Like the energy spectra, the phase spectra may be represented in different formats in the reference library, e.g. as a set of phase angle values associated with discrete frequency values or harmonic numbers, or as a phase function representing phase angle versus frequency/harmonic number.

From the above, it should be understood that the energy and phase data that are stored the reference library may be used to generate the predicted signal profile. Each energy value in the energy data corresponds to an amplitude of a sinusoid with a given frequency (the frequency associated with the energy value), wherein the phase value for the given frequency indicates the proper phase angle of the sinusoid. This method of preparing the predicted signal profile by combining (typically adding) sinusoids of appropriate frequency, amplitude and phase angle allows the predicted signal profile to include all harmonics of the pump frequency within a desired frequency range.

When a predicted signal profile is to be generated, the reference library is first searched based on a current value of one or more system parameters, such as the current pump frequency. If no exact match is found in the reference library, a combination process may be executed to generate the predicted signal profile. For example, the two closest matching pump frequencies may be identified in the reference library and the associated energy and phase data may be retrieved and combined to form the predicted signal profile. The combination may be done by interpolating the energy data and the phase data. In the example of FIGS. 15(a)-15(d), an interpolated energy value may be calculated for each harmonic number, and similarly an interpolated phase value may be calculated for each harmonic number. Any type of interpolation function may be used, be it linear or non-linear.

In the first, second and third embodiments, one and the same pressure wave sensor is suitably used in both the reference measurement and the actual monitoring process. Alternatively, different pressure wave sensors may be used, provided that the pressure wave sensors yield identical signal responses with respect to the pump pulses or that the signal responses may be matched using a known mathematical relationship.

To further improve the first, second and third embodiments, the process of generating the predicted signal profile may also involve compensating for other potentially relevant factors that differ between the reference measurement and the current operational state. These so-called confounding factors may comprise one or more of the system parameters listed above, such as absolute average venous and arterial pressures, temperature, blood hematocrit/viscosity, gas volumes, etc. This compensation may be done with the use of predefined compensation formulas or look-up tables.

In further variations, the second and third embodiments may be combined, e.g. in that the reference library stores not only energy and phase data, but also reference profiles, in association with system parameter value(s). When an exact match is found in the library, the reference profile is retrieved from the library and used as the predicted signal profile, otherwise the predicted signal profile is obtained by retrieving and combining (e.g. interpolating) the energy and phase data, as in the third embodiment. In a variant, the predicted signal profile u(n) at the current pump frequency v is obtained by:

$$u(n)=r_i(n)-r^r_i(n)+r^v(n),$$

wherein $r_i(n)$ denotes a reference profile that is associated with the closest matching pump frequency $v_i$ in the reference library, $r^r_i(n)$ denotes a reference profile that is reconstructed from the energy and phase data associated with the closest matching pump frequency $v_i$ in the reference library, and $r^v(n)$ denotes an estimated reference profile at the current pump frequency v. The estimated reference profile $r^v(n)$ may be obtained by applying predetermined functions to estimate the energy and phase data, respectively, at the current pump frequency v based on the energy and phase data associated with the closest matching pump frequency $v_i$. With reference to FIGS. 15(b)-15(c), such a predetermined function may thus represent the change in energy data between different flow rates. Alternatively, the estimated reference profile $r^v(n)$ may be obtained by retrieving and combining (e.g. interpolating) energy and phase data for the two closest matching pump frequencies $v_i$ and $v_j$ as in the third embodiment.

In a further variant, the reference measurement is made during regular operation of the extracorporeal circuit 20, instead of or in addition to any reference measurements made before regular operation (e.g. during priming or simulated treatments with blood). This reference measurement may be made by obtaining the reference signal from a pressure wave sensor which is substantially isolated from the pressure waves originating from the patient's heart, and use the reference signal for generating the predicted signal profile (optionally after adjustment/modification for differences in confounding factors), which is then used for removing pump pulses from the pressure signal. For example, the reference signal may be obtained from the system sensor 4b (FIG. 1) which may be essentially isolated from the pressure waves originating from the patient's heart.

Simulations

As an alternative to the use of reference measurements, the predicted signal profile may be obtained directly through simulations, i.e. calculations using a mathematical model of the extracorporeal circuit 20, based on current state information indicating the current operational state of the system. Such current state information may include a current value of one or more of the above-mentioned system parameters. The model may be based on known physical relationships of the system components (or via an equivalent representation, e.g. by representing the system as an electrical circuit with fluid flow and pressure being given by electrical current and voltage, respectively). The model may be expressed, implicitly or explicitly, in analytical terms. Alternatively, a numerical model may be used. The model may be anything from a complete physical description of the system to a simple function. In one example, such a simple function may convert data on the instantaneous angular velocity of the pump rotor 3' to a predicted signal profile, using empirical or theoretical data. Such data on the instantaneous angular velocity might be obtained from the pump sensor 26 in FIG. 1.

In another embodiment, simulations are used to generate reference profiles for different operational states of the system. These reference profiles may then be stored in a reference library, which may be accessed and used in the same way as described above for the second and third embodiments. It is also to be understood that reference profiles (and/or corresponding energy and phase angle data) obtained by simulations may be stored together with reference profiles (and/or corresponding energy and phase angle data) obtained by reference measurement.

V. Time Domain Filtering

There are several different ways of removing one or more pump pulses from the pressure/input signal, using a predicted signal profile of the pump pulses (e.g. obtained as described in Section IV above). Here, two different removal processes will be described: Single Subtraction and Adaptive Filtering. Of course, the description of removal processes and their implementations is not comprehensive (neither of the different alternatives, nor of the implementations), which is obvious to a person skilled in the art.

Depending on implementation, the predicted signal profile may be input to the removal process as is, or the predicted signal profile may be duplicated to construct an input signal of suitable length for the removal process.

Single Subtraction

In this removal process, a single predicted signal profile is subtracted from the pressure signal. The predicted signal profile may be shifted and scaled in time and scaled in amplitude in any way, e.g. to minimize the error of the removal. Different minimization criterions may be used for such an auto-scaling, e.g., minimizing the sum of the squared errors, or the sum of the absolute errors. Alternatively or additionally, the predicted signal profile is shifted in time based on the -mentioned pump pulse timing (cf. Section IV), i.e timing information that indicates the expected timing of the pump pulse(s) in the pressure signal.

One potential limitation of this removal process is that the relationship between different frequencies in the predicted signal profile is always the same, since the process only shifts and scales the predicted signal profile. Thus, it is not possible to change the relationship between different harmonic frequencies, neither is it possible to use only some of the frequency content in the predicted signal profile and to suppress other frequencies. To overcome this limitation, adaptive filtering may be used since it uses a linear filter before subtraction, e.g. as described in the following.

Adaptive Filtering

Figure 16:
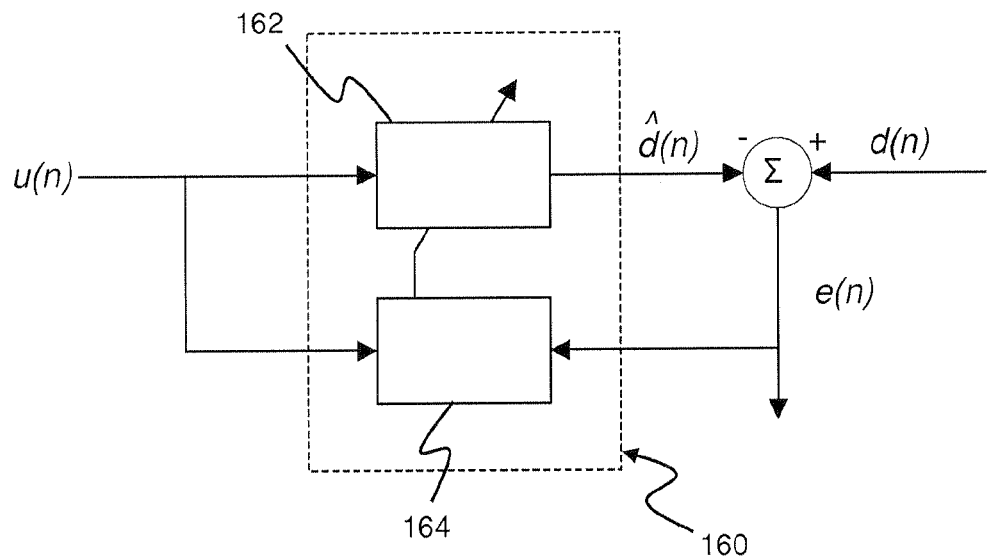
FIG. 16 is a schematic view of an adaptive filter structure operable to filter a pressure signal based on a predicted signal profile.

FIG. 16 is a schematic overview of an adaptive filter 160 and an adaptive filter structure which is designed to receive the predicted signal profile u(n) and a pressure signal d(n), and to output an error signal e(n) which forms the aforesaid monitoring signal in which the pump pulses are removed.

Adaptive filters are well-known electronic filters (digital or analog) that self-adjust their transfer function according to an optimizing algorithm. Specifically, the adaptive filter 160 includes a variable filter 162, typically a finite impulse response (FIR) filter of length M with filter coefficients w(n).

Even if adaptive filters are known in the art, they are not readily applicable to cancel the pump pulses in the pressure signal d(n). In the illustrated embodiment, this has been achieved by inputting the predicted signal profile u(n) to the variable filter 162, which processes the predicted signal profile u(n) to generate an estimation signal $\hat{d}(n)$, and to an adaptive update algorithm 164, which calculates the filter coefficients of the variable filter 162 based on the predicted signal profile u(n) and the error signal e(n). The error signal e(n) is given by the difference between the pressure signal d(n) and the estimation signal $\hat{d}(n)$.

Basically, the calculation of the error signal e(n) involves a subtraction of the predicted signal profile u(n) from the pressure signal d(n), since each of the filter coefficients operates to shift and possibly re-scale the amplitude of the predicted signal profile u(n). The estimation signal $\hat{d}(n)$, which is subtracted from the pressure signal d(n) to generate the error signal e(n), is thus formed as a linear combination of M shifted and amplitude-scaled predicted signal profiles u(n).

The adaptive update algorithm 164 may be implemented in many different ways, some of which will be described below. The disclosure is in no way limited to these examples, and the skilled person should have no difficulty of finding further alternatives based on the following description.

There are two main approaches to adaptive filtering: stochastic and deterministic. The difference lies in the minimization of the error signal e(n) by the update algorithm 164, where different minimization criteria are obtained whether e(n) is assumed to be stochastic or deterministic. A stochastic approach typically uses a cost function J with an expectation in the minimization criterion, while a deterministic approach typically uses a mean. The squared error signal $e^2(n)$ is typically used in a cost function when minimizing e(n), since this results in one global minimum. In some situations, the absolute error |e(n)| may be used in the minimization, as well as different forms of constrained minimizations. Of course, any form of the error signal may be used, however convergence towards a global minimum is not always guaranteed and the minimization may not always be solvable.

In a stochastic description of the signal, the cost function may typically be according to, $$J(n)=E\{|e(n)|^2\},$$

and in a deterministic description of the signal the cost function may typically be according to, $$J(n)=\Sigma e^2(n).$$

The pump pulses will be removed in the estimation signal $\hat{d}(n)$ when the error signal e(n) (cost function J(n)) is minimized. Thus, the error signal e(n) will be cleaned from pump pulses while retaining the heart pulses, once the adaptive filter 160 has converged and reached the minimum error.

In order to obtain the optimal filter coefficients w(n) for the variable filter 162, the cost function J needs to be minimized with respect to the filter coefficients w(n). This may be achieved with the cost function gradient vector $\nabla J$, which is the derivative of J with respect to the different filter coefficients $w_0, w_1, \ldots, w_{M-1}$. Steepest Descent is a recursive method (not an adaptive filter) for obtaining the optimal filter coefficients that minimize the cost function J. The recursive method is started by giving the filter coefficients an initial value, which is often set to zero, i.e., w(0)=0. The filter coefficients is then updated according to, $$w(n+1) = w(n) + \frac{1}{2}\mu[-\nabla J(n)],$$

where w is given by, $$w = [w_0 \quad w_1 \quad \ldots \quad w_{M-1}]^T \quad M \times 1.$$

Furthermore, the gradient vector $\nabla J$ points in the direction in which the cost is growing the fastest. Thus, the filter coefficients are corrected in the direction opposite to the gradient, where the length of the correction is influenced through the step size parameter µ. There is always a risk for the Steepest Descent algorithm to diverge, since the algorithm contains a feedback. This sets boundaries on the step size parameter µ in order to ensure convergence. It may be shown that the stability criterion for the Steepest Descent algorithm is given by, $$0 < \mu < \frac{2}{\lambda_{max}}$$

where $\lambda_{max}$ is the largest eigenvalue of R, the correlation matrix of the predicted signal profile u(n), given by $$R = E[\bar{u}(n)\bar{u}^T(n)] = \begin{bmatrix} r(0) & r(1) & \cdots & r(M-1) \\ r(1) & r(0) & & r(M-2) \\ \vdots & \vdots & \ddots & \vdots \\ r(M-1) & r(M-2) & \cdots & r(0) \end{bmatrix},$$

where $w$ is given by, $$\bar{u}(n) = [\, u(n) \quad u(n-1) \quad \cdots \quad u(n-M+1)\,]^T \quad M \times 1.$$

If the mean squared error (MSE) cost function (defined by $J=E\{|e(n)^2|\}$) is used, it may be shown that the filter coefficients are updated according to, $$w(n+1)=w(n)+E[\bar{u}(n)e(n)],$$

where e(n) is given by, $$e(n)=d(n)-\bar{u}^T(n)w(n).$$

The Steepest Descent algorithm is a recursive algorithm for calculation of the optimal filter coefficients when the statistics of the signals are known. However, this information is often unknown. The Least Mean Squares (LMS) algorithm is a method that is based on the same principles as the Steepest Descent algorithm, but where the statistics is estimated continuously. Thus, the LMS algorithm is an adaptive filter, since the algorithm is able to adapt to changes in the signal statistics (due to continuous statistic estimations), although the gradient may become noisy. Because of the noise in the gradient, the LMS algorithm is unlikely to reach the minimum error $J_{min}$, which the Steepest Descent algorithm does. Instantaneous estimates of the expectation are used in the LMS algorithm, i.e., the expectation is removed. Thus, for the LMS algorithm, the update equation of the filter coefficients becomes $$w(n+1)=w(n)+\mu\bar{u}(n)e(n).$$

The convergence criterion of the LMS algorithm is the same as for the Steepest Descent algorithm. In the LMS algorithm, the step size is proportional to the predicted reference profile u(n), i.e., the gradient noise is amplified when the predicted reference profile is strong. One solution to this problem is to normalize the update of the filter coefficients with $$\|\bar{u}(n)\|^2 = \bar{u}^T(n)\bar{u}(n).$$

The new update equation of the filter coefficients is called the Normalized LMS, and is given by $$w(n+1) = w(n) + \frac{\tilde{\mu}}{a + \|\bar{u}(n)\|^2}\bar{u}(n)e(n),$$

where $0<\tilde{\mu}<2$, and a is a positive protection constant.

There are many more different alternatives to the LMS algorithm, where the step size is modified. One of them is to use a variable adaptation step, $$w(n+1)=w(n)+\alpha(n)\bar{u}(n)e(n),$$

where $\alpha(n)$ for example may be, $$\alpha(n) = \frac{1}{n+c},$$

where c is a positive constant. It is also possible to choose independent adaptation steps for each filter coefficient in the LMS algorithm, e.g., according to, $$w(n+1)=w(n)+A\bar{u}(n)e(n),$$

where A is given by, $$A = \begin{bmatrix} \alpha_1 & 0 & 0 & \cdots & 0 \\ 0 & \alpha_2 & 0 & \cdots & 0 \\ 0 & 0 & \alpha_3 & \cdots & 0 \\ \vdots & \vdots & \vdots & \ddots & \vdots \\ 0 & 0 & 0 & \cdots & \alpha_M \end{bmatrix}.$$

If instead the following cost function $$J(n)=E\{|e(n)|\}$$

is used, then the update equation becomes $$w(n+1)=w(n)+\alpha\,\mathrm{sign}[e(n)]\bar{u}(n).$$

This adaptive filter is called the Sign LMS, which is used in applications with extremely high requirements on low computational complexity.

Another adaptive filter is the Leaky LMS, which uses a constrained minimization with the following cost function $$J(n)=E\{|e(n)|^2\}+\alpha\|w(n)\|^2.$$

This constraint has the same effect as if white noise with variance a was added to the predicted signal profile u(n). As a result, the uncertainty in the predicted signal profile u(n) is increased, which tends to hold the filter coefficients back. The Leaky LMS is preferably used when R, the correlation matrix of u(n), has one or more eigenvalues equal to zero. However, in systems without noise, the Leaky LMS makes performance poorer. The update equation of the filter coefficients for the Leaky LMS is given by, $$w(n+1)=(1-\mu\alpha)w(n)+\mu\bar{u}(n)e(n).$$

Instead of minimizing the MSE cost function as above, the Recursive Least Squares (RLS) adaptive filter algorithm minimizes the following cost function $$J(n) = \sum_{i=1}^{n} \lambda^{n-i}|e(i)|^2,$$

where $\lambda$ is called forgetting factor, $0<\lambda\leq 1$, and the method is called Exponentially Weighted Least Squares. It may be shown that the update equations of the filter coefficients for the RLS algorithm are, after the following initialization $$w(0)=0_{M\times 1}$$

$$P(0)=\delta^{-1}I_{M\times M}$$

where $I_{M\times M}$ is the identity matrix M×M, given according to $$k(n) = \frac{\lambda^{-1}P(n-1)\bar{u}(n)}{1+\lambda^{-1}\bar{u}^T(n)P(n-1)\bar{u}(n)}$$

$$\xi(n) = d(n) - w^T(n-1)\bar{u}(n)$$

$$w(n) = w(n-1) + k(n)\xi(n)$$

$$P(n) = \lambda^{-1}P(n-1) - \lambda^{-1}k(n)\bar{u}^T(n)P(n-1),$$

where $\delta$ is a small positive constant for high signal-to-noise ratio (SNR), and a large positive constant for low SNR, $\delta << 0.01 \sigma_u^2$, and $\xi(n)$ corresponds to e(n) in the preceding algorithms. During the initialization phase the following cost function $$J(n) = \sum_{i=1}^{n} \lambda^{n-i} |e(i)|^2 + \delta \lambda^n \|w(n)\|^2,$$

is minimized instead, due to the use of the initialization $P(0) = \delta^{-1} I$. The RLS algorithm converges in approximately 2M iterations, which is considerably faster than for the LMS algorithm. Another advantage is that the convergence of the RLS algorithm is independent of the eigenvalues of R, which is not the case for the LMS algorithm.

Several RLS algorithms running in parallel may be used with different $\lambda$, and $\delta$, which may be combined in order to improve performance, i.e., $\lambda=1$ may also be used in the algorithm (steady state solution) with many different $\delta$:s.

It should be noted that both the LMS algorithm and the RLS algorithm may be implemented in fixed-point arithmetic, such that they may be run on a processor that has no floating point unit, such as a low-cost embedded microprocessor or microcontroller.

Irrespective of implementation, the performance of the adaptive filter 160 may be further improved by switching the adaptive filter 160 to a static mode, in which the update algorithm 164 is disabled and thus the filter coefficients of the filter 162 are locked to a current set of values. The switching of the adaptive filter 160 may be controlled by an external process that analyses the heart pulses in the error signal e(n), typically in relation to the above-mentioned pump pulse timing, which may be obtained from the pressure signal, a reference signal (see above), a dedicated pulse sensor, a control unit for the blood pump, etc. The adaptive filter 160 may be switched into the static mode if the external process reveals that the rate of heart pulses starts to approach the rate of the pump pulses and/or that the amplitude of the heart pulses is very weak (in relation to an absolute limit, or in relation to a limit given by the amplitude of the pump pulses). The adaptive filter 160 may remain in static mode for a predetermined time period, or until released by the external process.

In a variant, a predicted signal profile of the heart pulses (denoted "predicted heart profile") is used as input signal to the adaptive filter 160 (instead of the predicted signal profile of the pump pulses), and the monitoring signal is formed by the estimation signal d̂(n) (instead of the error signal e(n)). The foregoing discussion with respect to adaptive filters is equally applicable to this variant.

Difference embodiments and examples of techniques for obtaining such a predicted heart profile is disclose in Section VI below, together with techniques for obtaining the primary timing data used in the monitoring (cf. step 304 in FIG. 3). In addition to Section VI, reference is also made to WO2009/156174, which is incorporated herein in its entirety by this reference.

VI. Obtaining Timing Data and Predicted Heart Profile

Timing Data

The timing data (cf. step 304 in FIG. 3) may be obtained in a plurality of different ways. All of these ways typically involve detecting pulses in an input signal, and estimating the occurrence time of each pulse in the input signal. In essence, any known pulse detection technique may be used, be it digital or analog. Such techniques include, but are not limited to: convolution/matching with static or dynamic pulse templates, peak detection (e.g. via detection of local maxima/minima), and thresholding. Many different input signals may be used, as will exemplified in following.

For example, the timing data may be extracted from the output signal of a pulse sensor coupled to the patient. The output signal may indicate individual heart pulses or an average time between heart pulses. In either case, a predicted time point for a heart pulse in the pressure signal may be calculated based on the output signal of the pulse sensor and a known difference in arrival time between the pulse sensor and the pressure wave sensor that generates the pressure signal. The pulse sensor may sense the pressure waves that are generated in the patient's cardiovascular system by the heartbeats, or it may directly reflect the beat generation process in patient's heart. In such an application, the timing data may be provided by any conventional pulse sensor such as a pulse watch, a photoplethysmograph (PPG) such as a pulse oximeter, an electrocardiograph (ECG), etc.

Alternatively, the timing data may be obtained by sequentially identifying the heart pulses in the monitoring signal. Such a process may, but need not, involve a step of predicting the time point for subsequent heart pulse(s) based on the time difference between the two most recently detected heart pulses.

Alternatively, the timing data may be obtained from one or more reference signals originating from a reference sensor in the extracorporeal circuit. The reference sensor may sense the pressure waves that are generated in the patient's cardiovascular system by the heartbeats and propagated into the extracorporeal circuit, or it may directly reflect the beat generation process in patient's heart.

One example of such a reference sensor is an ECG apparatus which is configured to detect the patient's electrical voltages transmitted from the access devices 1, 14 to dedicated electrodes in the connection system C or the extracorporeal circuit 20 via the blood, via electrically conductive blood tubing or on other conductive pathways. The use of such an ECG apparatus for the purpose of detecting disconnection of an access device from the blood access of a patient is disclosed in US2007/0000847, which is incorporated herein by this reference.

Another example of such a reference sensor is a pressure wave sensor in the extracorporeal circuit 20 (FIG. 1). For example, if the monitoring signal is generated from a pressure signal acquired from one of the pressure sensors 4a-4c, the reference signal may be acquired from another of the pressure sensors 4a-4c. The reference signal may be processed for detection of at least one heart pulse (e.g. according to Section III). The time point of the detected heart pulse in the reference signal may then be converted to a predicted time point in the monitoring signal/evaluation segment using a known/measured difference in pulse arrival/transit time between the reference sensor and the pressure sensor that provides the pressure signal for monitoring. Thus, in one embodiment, the difference in transit time is given by a fixed and predefined value.

In another embodiment, the difference in transit time between a bloodline on the arterial side and a bloodline on the venous side in the extracorporeal circuit 20 is determined based on the actual arterial and venous pressures (absolute, relative, or average), which may be derived from any suitable sensor in the extracorporeal circuit (including the pressure sensors 4a-4c). The transit time decreases if the pressure increases, i.e., high pressure equals short transit time. During operation of the extracorporeal circuit 20, the venous pressure should be higher than the arterial pressure, and thus the transit time should be shorter in the venous bloodline compared to the transit time in the arterial bloodline. The difference in transit time may be determined based on, e.g., a physical model or a look-up table. The model/table may not only include information about pressure (absolute, relative, or average), but also information about material (elasticity, plasticity, etc), geometry (length, diameter, wall thickness, etc), temperature (both fluids and ambient temperature), mechanical factors (clamp, tension, actuators, kinking/occlusion, etc), fluid properties (viscosity, water/blood, chemical composition, etc), etc. The thus-determined difference in transit time may then be used to relate a time point of a detected heart pulse in the reference signal from the arterial/venous pressure sensor to a predicted time point in the monitoring signal/evaluation segment originating from the venous/arterial pressure sensor.

In a variant, an improved estimation of the timing data may be obtained by aligning and combining a first reference signal (e.g. derived from the venous/arterial pressure signal) with a second reference signal (e.g. derived from the arterial/venous pressure signal), to thereby calculate an average time-dependent reference signal with improved SNR. The first and second reference signals are suitably filtered for removal of interference pulses (e.g. according to Section III). The aligning may be based on the aforesaid difference in transit time, given by the actual arterial and venous pressures (absolute, relative, or average). By identifying one or more heart pulses in the average reference signal, an improved estimation of the timing data may be obtained.

Alternatively or additionally, to potentially improve the precision of the timing data, the timing data may be obtained by intermittently stopping the pulse generator(s) in the extracorporeal circuit 20, while identifying at least one heart pulse in the monitoring signal, the reference signal or the first and second reference signals, as applicable.

Optionally, the process of obtaining timing data based on an identified heart pulse in the monitoring signal or the reference signal(s) may involve validating the identified heart pulse (a candidate pulse) against a temporal criterion. Such a temporal criterion may, e.g., indicate an upper limit and/or a lower limit for the time difference between the time point for the candidate pulse and one or more previously identified (and suitably validated) heart pulses. These limits may be fixed, or they may be set dynamically in relation to a preceding time difference. Any candidate pulse that violates the temporal criterion may be removed/discarded from use in obtaining the timing data.

Figure 17:
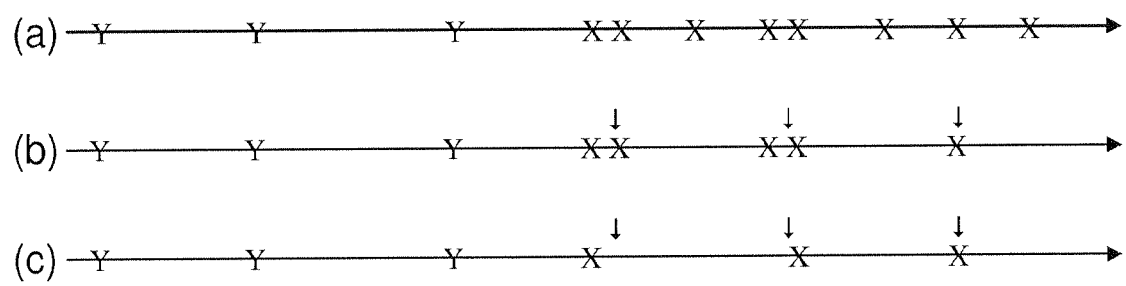
FIGS. 17(a)-17(c) illustrate processing of candidate pulses identified in a reference signal, for generation of timing data.

FIG. 17 illustrates such a validation method for processing of candidate pulses. In the illustrated example, it is assumed that each candidate pulse is associated with a probability value, which indicates the likelihood that the candidate pulse is a heart pulse. The probability value may be given by a magnitude the candidate pulse (e.g. maximum amplitude, integrated area, etc) or a measure resulting from an identification process (e.g. a correlation value). FIG. 17(*a*) illustrates a sequence of candidate pulses (denoted by X), as well as a sequence of preceding heart pulses (denoted by Y), laid out on a time axis. In a first validation step, predicted time points (arrows 1 in FIG. 17(*b*)) are calculated based on the heart pulses Y. In a second validation step, a first temporal criterion is applied to remove/discard any candidate pulses that lie too far from the predicted time points, as also shown in FIG. 17(*b*). In a third validation step, a second temporal criterion is applied to retain only the candidate pulse with the largest probability value among any candidate pulses that lie too close to each other, as shown in FIG. 17(*c*).

In all of the above embodiments and examples, the monitoring signal and the reference signal(s) may be up-sampled (e.g. by means of interpolation) before being processed for determining the timing data. This may increase the accuracy of the timing data.

Predicted Heart Profile

The predicted heart profile may be generated as an average of a number of recordings of heart pulses. For example, it may be generated by aligning and combining (adding, averaging, etc) a number of heart pulse segments in the monitoring signal/evaluation segment, before and/or during the monitoring process. The averaging may or may not use the timing data to align the heart pulse segments.

To improve the signal quality of the predicted heart profile, with or without averaging, the pressure signal may be acquired while the blood pump is stopped, whereby the pressure signal is free of pump pulses. Thus, the blood pump may be intermittently stopped during the monitoring process for calculation of an updated signal profile of the heart pulses.

In another variant, the predicted heart profile is obtained from the above-mentioned reference signal, which may be used for deriving the timing data.

Alternatively, the predicted heart profile may be pre-generated, e.g. by averaging recordings of heart pulses from a number of similar extracorporeal circuits. Optionally, such a pre-generated signal profile may be adapted to specifics of the extracorporeal circuit to be used for monitoring, by applying a mathematical model taking into account arrangement-specific parameters, such a type of blood vessel access, connection system, flow rate, fluid characteristics, etc. Alternatively, the predicted heart profile may be obtained entirely by mathematical modelling based on arrangement-specific parameters. According to yet another alternative, a standard profile is used as predicted heart profile, e.g. a bell-shaped function such as a Gaussian distribution function.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

Some of the filtering techniques described above in relation to step 1003' and/or step 1003" may automatically be achieved by down-sampling of the pressure signal, since the desired filtering may be achieved by the anti-aliasing filter included in a down-sampling signal processing algorithm. Additionally, some of the above-described filtering techniques may also be achieved directly in hardware, e.g., in the Analog-to-Digital (A/D) conversion by choosing an appropriate sampling frequency, i.e. due to the anti-aliasing filter which is applied before sampling.

The extracorporeal circuit may include any type of pumping device, not only rotary peristaltic pumps as disclosed above, but also other types of positive displacement pumps, such as linear peristaltic pumps, diaphragm pumps, as well as centrifugal pumps.

Embodiments of the invention are also applicable when the connection system comprises a single access device, such as in so-called single needle treatment.

The embodiments of the invention are applicable to all types of extracorporeal blood flow circuits in which blood is taken from the systemic blood circuit of the patient to have a process applied to it before it is returned to the patient. Such blood flow circuits include circuits for hemodialysis, hemofiltration, hemodiafiltration, plasmapheresis, apheresis, extracorporeal membrane oxygenation, assisted blood circulation, extracorporeal liver support/dialysis, and blood fraction separation (e.g. cells) of donor blood. The inventive technique is likewise applicable for monitoring in other types of extracorporeal fluid circuits, such as circuits for blood transfusion, infusion, as well as heart-lung-machines.

Furthermore, the monitoring process may operate on more than one monitoring signal, with each monitoring signal being generated from a pressure signal acquired from a respective pressure wave sensor. In all embodiments, each monitoring signal may be generated from more than one pressure signal, e.g. by combining (e.g. averaging) corresponding heart pulses in (filtered) pressure signals (e.g. as described above in relation to the first and second reference signals).

In a specific embodiment, the monitoring technique may be dynamically adjusted based on the magnitude of the pump pulses and/or the heart pulses in the pressure signal/monitoring signal/reference signal. The dynamic adjustment may e.g. affect the process for obtaining timing data, the process for calculating the parameter value, or the process for removing interference pulses. In one example, the surveillance device receives two or more pressure signals (from different pressure wave sensors), and monitors the magnitude of the heart pulses in each pressure signal. The surveillance device may be configured to dynamically select, based on the magnitude of the heart pulses in the different pressure signals, one or more pressure signals to be used for the generation of the monitoring signal, and/or for the determination of the timing data, and/or for the determination of the predicted heart profile. The magnitude of the heart pulses may be compared to a predetermined absolute limit, or the magnitude of the heart pulses may be compared between the different pressure signals. In another example, the surveillance device dynamically selects a technique for the removal of interference pulses, based on the magnitude of the heart pulses in the pressure signal/monitoring signal. In yet another example, the surveillance device dynamically selects the parameter value to be calculated and/or the procedure for calculating the parameter value, based on the magnitude of the heart pulses in the pressure signal/monitoring signal. In the above examples, if the magnitude of the pump pulses and the heart pulses are covariant entities, the dynamic adjustment may alternatively be based on the magnitude of pump pulses, or the magnitude of a combination of pump and heart pulses.

In one embodiment, the blood pump is regularly (intermittently or periodically) stopped, and the pressure signal and/or reference signal is analysed for determination of at least one of shape, amplitude, frequency and phase (timing) of heart pulses. This embodiment may, e.g, be used for the dynamic control of the monitoring technique, as described above. Alternatively or additionally, if the magnitude of the heart pulse(s) detected during such a stop is smaller than a certain limit (chosen with a margin for safe detection), an alert on "uncertain detection" may be issued. Alternatively, if the magnitude is smaller than another limit, the blood pump may be actively controlled to be stopped at specific time intervals, where the information obtained during each stop may be used to modify the monitoring technique. For example, the thus-obtained information may be used to change (or add) threshold values in the procedures for calculating the parameter value, or to determine if an alternative parameter value should be calculated or an alternative calculation procedure should be used. In another example, if the thus-obtained information indicates the rate of heart pulses, a dedicated bandpass filter (e.g. centred on the thus-obtained pulse rate) may be operated on the reference/pressure signal to further improve the input to the process for obtaining timing data and/or the process for calculating the parameter value based on the monitoring signal. In one embodiment, such a bandpass filter is applied if the rates of the pump pulses and the heart pulses are found to differ by more than a certain limit, e.g. about 10%.

The above-described monitoring process may be executed by a surveillance device (cf. 25 in FIG. 1), which may be implemented by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The surveillance device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software, and the adjustment factors, may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The surveillance device may include one or more communication interfaces, such as a serial interface, a parallel interface, a USB interface, a wireless interface, a network adapter, etc, as well as one or more data acquisition devices, such as an A/D converter. The special-purpose software may be provided to the surveillance device on any suitable computer-readable medium, including a record medium, a read-only memory, or an electrical carrier signal.

It is also conceivable that some (or all) method steps are fully or partially implemented by dedicated hardware, such as an FPGA, an ASIC, or an assembly of discrete electronic components (resistors, capacitors, operational amplifier, transistors, filters, etc), as is well-known in the art.

In the following, a set of items are recited to summarize some aspects and embodiments of the invention as disclosed in the foregoing.

Item 1. A device for monitoring a cardiovascular property of a subject, wherein the device comprises an input (28) configured to obtain measurement data from a primary pressure wave sensor (4*a*-4*c*) which is arranged to detect pressure waves in an extracorporeal fluid circuit (20) which is connected in fluid communication with the cardiovascular system of the subject, wherein the device further comprises a signal processor (29) configured to:

generate a time-dependent monitoring signal based on the measurement data, such that the monitoring signal comprises a sequence of heart pulses, wherein each heart pulse represents a pressure wave originating from a heart beat in the subject;

determine beat classification data for each heart pulse in the monitoring signal; and calculate, based at least partly on the beat classification data, a parameter value indicative of the cardiovascular property.

Item 2. The device of item 1, wherein the beat classification data distinguishes between heart pulses originating from normal heart beats and heart pulses originating from ectopic heart beats.

Item 3. The device of item 1 or 2, wherein the signal processor (29) is configured to determine the beat classification data based on at least one of primary timing data, which represents the occurrence time of each heart pulse in the monitoring signal, and shape data, which represents the shape of each heart pulse in the monitoring signal.

Item 4. The device of item 3, wherein the signal processor (29) is configured to determine the beat classification data by: processing the monitoring signal to extract at least one shape feature which is representative of the temporal shape of each heart pulse.

Item 5. The device of item 3 or 4, wherein the signal processor (29) is configured to determine the beat classification data based on a combination of a plurality of different shape features extracted from each heart pulse.

Item 6. The device of any one of items 3-5, wherein the signal processor (29) is configured to determine the beat classification data by: extracting at least part of a temporal profile of each heart pulse, and matching said at least part of the temporal profile against a set of templates.

Item 7. The device of any one of items 3-6, wherein the signal processor (29) is configured to determine the beat classification data by: obtaining, based on the primary timing data, time differences between heart pulses in the monitoring signal, and evaluating each time difference against a time interval criterion.

Item 8. The device of any one of items 3-7, wherein the signal processor (19) is configured to obtain the primary timing data by at least one of: processing the monitoring signal for identification of heart pulses, and processing a reference signal obtained via the input (28) from a reference sensor (4a-4c) in the extracorporeal circuit (20) or on the subject.

Item 9. The device of item 8, wherein the reference sensor is a pressure wave sensor.

Item 10. The device of item 9, wherein the signal processor (29) is configured to obtain the primary timing data by adjusting for a difference in transit time between the reference sensor (4a-4c) and the primary pressure wave sensor (4a-4c).

Item 11. The device of item 10, wherein the transit time is given by a predefined value.

Item 12. The device of item 10, wherein the signal processor (29) is configured to calculate the transit time based on a difference in fluid pressure between the locations of the reference sensor (4a-4c) and the primary pressure wave sensor (4a-4c).

Item 13. The device of item 8, wherein the reference sensor is an ECG sensor.

Item 14. The device of any one of items 8-12, wherein the signal processor (19) is configured to obtain the primary timing data by: identifying a set of candidate heart pulses in the monitoring signal or the reference signal; deriving a sequence of candidate time points based on the set of candidate heart pulses; validating the sequence of candidate time points against a temporal criterion; and calculating the timing data as a function of the thus-validated sequence of candidate time points.

Item 15. The device of any preceding item, wherein the signal processor (29) is configured to calculate the parameter value by: generating secondary timing data based on the beat classification data, the secondary timing data representing the occurrence times of the heart pulses for use in calculating the parameter value.

Item 16. The device of item 15, wherein the signal processor (29) is configured to, if the beat classification data identifies heart pulses originating from ectopic heart beats and if a selection criterion is met, generate the secondary timing data by estimating a corrected time point for each heart pulse that is classified as originating from an ectopic heart beat.

Item 17. The device of item 16, wherein the selection criterion indicates that the parameter value is at least one of heart rate and heart rate variability.

Item 18. The device of any one of items 15-17, wherein the signal processor (29) is configured to process the secondary timing data for calculation of the parameter value as a measure of at least one of heart rate variability and heart rate. The signal processor (29) may be configured to calculate the measure of heart rate variability by at least partly compensating for variations in transit time of the pressure waves originating from the heart beat in the subject, said variations originating from pressure variations in the extracorporeal fluid circuit (20) caused by at least one pumping device (3) in the extracorporeal fluid circuit (20).

Item 19. The device of any one of items 15-18, wherein the signal processor (29) is configured to, if the beat classification data identifies heart pulses originating from ectopic heart beats, process the beat classification data and the secondary timing data, for calculation of the parameter value as a measure of heart rate turbulence.

Item 20. The device of any one of items 15-19, wherein the signal processor (29) is configured to, if the beat classification data identifies heart pulses originating from ectopic heart beats, select, based on the beat classification data, a subset of the heart pulses in the monitoring signal and to generate the parameter value as a measure of the average temporal shape of the selected subset.

Item 21. The device of item 20, wherein the signal processor (29) is configured to generate the average temporal shape by: aligning and combining, based on the secondary timing data, the subset of the heart pulses.

Item 22. The device of any preceding item, wherein the signal processor (29) is configured to, if the beat classification data identifies heart pulses originating from ectopic heart beats, process the beat classification data for calculation of the parameter value as a count of ectopic heart beats.

Item 23. The device of any preceding item, wherein the measurement data comprises the sequence of heart pulses and at least one interference pulse, wherein the signal processor (29) is configured to generate the monitoring signal by processing the measurement data to essentially eliminate said at least one interference pulse.

Item 24. The device of item 23, wherein the signal processor (29) is configured to obtain a pulse profile (u(n)) which is a predicted temporal signal profile of the interference pulse, and to filter the measurement data in the time domain, using the pulse profile (u(n)), to essentially eliminate the interference pulse while retaining the sequence of heart pulses.

Item 25. The device of item 24, wherein the signal processor (29) is configured to subtract the pulse profile (u(n)) from the measurement data.

Item 26. The device of item 25, wherein the signal processor (29) is configured to, before subtracting the pulse profile (u(n)), adjust at least one of the amplitude, the time scale and the phase of the pulse profile (u(n)) with respect to the measurement data.

Item 27. The device of item 26, wherein the signal processor (29) is configured to minimize a difference between the pulse profile (u(n)) and the measurement data.

Item 28. The device of any one of items 25-27, wherein said at least one interference pulse originates from at least one pumping device (3) in the extracorporeal fluid circuit (20), and wherein the signal processor (29) is configured to subtract the pulse profile (u(n)) by adjusting a phase of the pulse profile (u(n)) in relation to the measurement data, wherein said phase is indicated by phase information obtained from at least one of: a pump rate sensor (25) coupled to said at least one pumping device (3), and a controller (24) for said at least one pumping device (3).

Item 29. The device of item 24, wherein the signal processor (29) comprises an adaptive filter (160) which is arranged to generate an estimation signal ($\hat{d}(n)$), based on the pulse profile (u(n)) and an error signal (e(n)) formed as a difference between the measurement data and the estimation signal ($\hat{d}(n)$), whereby the adaptive filter (160) is arranged to essentially eliminate said at least one interference pulse in the error signal (e(n)). Further, the adaptive filter (160) may be configured to generate the estimation signal ($\hat{d}(n)$) as a linear combination of M shifted pulse profiles (u(n)), and specifically the adaptive filter (160) may be configured to linearly combine M instances of the pulse profiles (u(n)), which are properly adjusted in amplitude and phase by the adaptive filter (30).

Item 30. The device of item 29, wherein the adaptive filter (160) comprises a finite impulse response filter (162) with filter coefficients that operate on the pulse profile (u(n)) to generate the estimation signal ($\hat{d}(n)$), and an adaptive algorithm (164) which optimizes the filter coefficients as a function of the error signal (e(n)) and the pulse profile (u(n)).

Item 31. The device of item 29 or 30, wherein the signal processor (29) is configured to control the adaptive filter (160) to lock the filter coefficients, based on a comparison of the rate and/or amplitude of the heart pulses to a limit value.

Item 32. The device of any one of items 24-31, wherein said at least one interference pulse originates from at least one pumping device (3) in the extracorporeal fluid circuit (20), and wherein the signal processor (29) is configured to, in a reference measurement, cause said at least one pumping device (3) to generate at least one interference pulse, and obtain the pulse profile (u(n)) from a reference signal generated by a reference sensor (4a-4c).

Item 33. The device of item 32, wherein said at least one pumping device (3) is operated to generate a sequence of interference pulses during the reference measurement, and wherein the pulse profile (u(n)) is obtained by identifying and combining a set of interference pulses in the reference signal.

Item 34. The device of item 32 or 33, wherein the signal processor (29) is configured to intermittently effect the reference measurement to update the pulse profile (u(n)) during operation of the extracorporeal fluid circuit (20).

Item 35. The device of any one of items 24-31, wherein said at least one interference pulse originates from at least one pumping device (3) in the extracorporeal fluid circuit (20), and wherein the signal processor (29) is configured to obtain the pulse profile (u(n)) based on a predetermined signal profile.

Item 36. The device of item 35, wherein the signal processor (29) is configured to modify the predetermined signal profile according to a mathematical model based on a current value of one or more system parameters of the extracorporeal fluid circuit (20).

Item 37. The device of item 24-31, wherein said at least one interference pulse originates from at least one pumping device (3) in the extracorporeal fluid circuit (20), and wherein the signal processor (29) is configured to obtain a current value of one or more system parameters of the extracorporeal fluid circuit (20), and to obtain the pulse profile (u(n)) as a function of the current value.

Item 38. The device of item 37, wherein the signal processor (29) is configured to obtain the pulse profile (u(n)) by identifying, based on the current value, one or more temporal reference profiles ($r_1(n)$, $r_2(n)$) in a reference database (DB); and obtaining the pulse profile (u(n)) based on said one or more temporal reference profiles ($r_1(n)$, $r_2(n)$).

Item 39. The device of item 38, wherein said one or more system parameters is indicative of a pumping rate of said at least one pumping device (3).

Item 40. The device of item 38 or 39, wherein each temporal reference profile ($r_1(n)$, $r_2(n)$) in the reference database (DB) is obtained by a reference measurement in the extracorporeal fluid circuit (20) for a respective value of said one or more system parameters.

Item 41. The device of item 37, wherein the signal processor (29) is configured to obtain the pulse profile (u(n)) by identifying, based on the current value, one or more combinations of energy and phase angle data in a reference database (DB); and obtaining the pulse profile (u(n)) based on said one or more combinations of energy and phase angle data.

Item 42. The device of item 41, wherein the signal processor (29) is configured to obtain the pulse profile (u(n)) by combining a set of sinusoids of different frequencies, wherein the amplitude and phase angle of each sinusoid is given by said one or more combinations of energy and phase angle data.

Item 43. The device of item 37, wherein the signal processor (29) is configured to obtain the pulse profile (u(n)) by inputting the current value into an algorithm which calculates the response of the primary pressure wave sensor (4a-4c) based on a mathematical model of the extracorporeal fluid circuit (20).

Item 44. The device of item 23, wherein the signal processor (29) is configured to obtain a pulse profile (u(n)) which is a predicted temporal signal profile of the heart pulse, and to filter the measurement data in the time domain, using the pulse profile (u(n)), to essentially eliminate the interference pulse while retaining the sequence of heart pulses.

Item 45. The device of item 44, wherein the signal processor (29) comprises an adaptive filter (160) which is arranged to generate an estimation signal ($\hat{d}(n)$), based on the pulse profile (u(n)) and an error signal (e(n)) formed as a difference between the measurement data and the estimation signal ($\hat{d}(n)$), whereby the adaptive filter (160) is arranged to essentially eliminate said at least one interference pulse in the estimation signal ($\hat{d}(n)$). The adaptive filter (160) may be configured to generate the estimation signal ($\hat{d}(n)$) as a linear combination of M shifted pulse profiles (u(n)), and specifically the adaptive filter (160) may be configured to linearly combine M instances of the pulse profile (u(n)), which are properly adjusted in amplitude and phase by the adaptive filter (30).

Item 46. The device of any preceding item, wherein the signal processor (29) implements a first process for generating the monitoring signal, a second process for obtaining primary timing data, and a third process for calculating the parameter value, wherein the signal processor (29) is further configured to evaluate the magnitude of the heart pulses in the monitoring signal, or in a reference signal obtained from a reference sensor (4a-4c), and to selectively control at least one of the first, second and third processes based on the magnitude of the heart pulses.

Item 47. The device of any preceding item, wherein the measurement data comprises the sequence of heart pulses and at least one interference pulse, which originates from at least one pumping device (3) in the extracorporeal fluid circuit (20), wherein the signal processor (29) is further configured to calculate a rate of heart pulses in the monitoring signal, or in a reference signal obtained from a reference sensor (4a-4c), and to cause a pumping frequency of said at least one pumping device (3) to be controlled in relation to the rate of heart pulses.

Item 48. The device of item 47, wherein the pumping frequency is controlled to shift the rate of interference pulses away from the rate of heart pulses.

Item 49. The device of item 47, wherein the pumping frequency is controlled to synchronize the rate of interference pulses with the rate of heart pulses, while applying a given phase difference between the interference pulses and the heart pulses.

Item 50. The device of any one of items 1-47, wherein the extracorporeal fluid circuit (20) comprises at least one pumping device (3) which, when in an operating state, generates interference pulses in the measurement data, wherein the device is configured to obtain the measurement data while said at least one pumping device (3) is intermittently set in a disabled state.

Item 51. The device of any preceding item, wherein the cardiovascular property is at least one of an arterial status of the cardiovascular system of the subject, a degree of calcification in the cardiovascular system of the subject, a status of a blood vessel access used for connecting the extracorporeal fluid circuit (20) to the cardiovascular system of the subject, a heart rate variability, a heart rate, a heart rate turbulence, an ectopic beat count, and an origin of ectopic beats.

Item 52. A device for monitoring a cardiovascular property of a subject, said device comprising:

means (400) for obtaining measurement data from a primary pressure wave sensor (4a-4c) which is arranged to detect pressure waves in an extracorporeal fluid circuit (20) which is connected in fluid communication with the cardiovascular system of the subject;

means (401) for generating a time-dependent monitoring signal based on the measurement data, such that the monitoring signal comprises a sequence of heart pulses, wherein each heart pulse represents a pressure wave originating from a heart beat in the subject;

means (403) for determining beat classification data for each heart pulse in the monitoring signal; and means (404) for calculating, based at least partly on the beat classification data, a parameter value indicative of the cardiovascular property.

Embodiments of the device as set forth in item 52 may correspond to the embodiments of the device as set forth in items 2-51.

Item 60. An apparatus for blood treatment, comprising an extracorporeal blood flow circuit (20) adapted for connection to the vascular system of a subject and operable to circulate blood from the subject through a blood processing device (6) and back to the subject, and the device as set forth in any one of items 1-52.

Item 70. A method for monitoring a cardiovascular property of a subject, said method comprising:

obtaining measurement data from a primary pressure wave sensor (4a-4c) which is arranged to detect pressure waves in an extracorporeal fluid circuit (20) which is connected in fluid communication with the cardiovascular system of the subject;

generating a time-dependent monitoring signal based on the measurement data, such that the monitoring signal comprises a sequence of heart pulses, wherein each heart pulse represents a pressure wave originating from a heart beat in the subject;

determining beat classification data for each heart pulse in the monitoring signal; and calculating, based at least partly on the beat classification data, a parameter value indicative of the cardiovascular property.

Item 71. The method of item 69, wherein the beat classification data distinguishes between heart pulses originating from normal heart beats and heart pulses originating from ectopic heart beats.

Item 72. The method of item 70 or 71, wherein the beat classification data is determined based on at least one of primary timing data, which represents the occurrence time of each heart pulse in the monitoring signal, and shape data, which represents the shape of each heart pulse in the monitoring signal.

Item 73. The method of item 72, wherein the beat classification data is determined by: processing the monitoring signal to extract at least one shape feature which is representative of the temporal shape of each heart pulse.

Item 74. The method of item 72 or 73, wherein the beat classification data is determined based on a combination of a plurality of different shape features extracted from each heart pulse.

Item 75. The method of any one of items 72-74, wherein the beat classification data is determined by: extracting at least part of a temporal profile of each heart pulse, and matching said at least part of the temporal profile against a set of templates.

Item 76. The method of any one of items 72-75, wherein the beat classification data is determined by: obtaining, based on the primary timing data, time differences between heart pulses in the monitoring signal, and evaluating each time difference against a time interval criterion.

Item 77. The method of any one of items 72-76, further comprising: obtaining the primary timing data by at least one of: processing the monitoring signal for identification of heart pulses, and processing a reference signal obtained via the input (28) from a reference sensor (4a-4c) in the extracorporeal circuit (20) or on the subject.

Item 78. The method of item 77, wherein the reference sensor is a pressure wave sensor.

Item 79. The method of item 78, wherein said obtaining the primary timing data comprises: adjusting for a difference in transit time between the reference sensor (4a-4c) and the primary pressure wave sensor (4a-4c).

Item 80. The method of item 79, wherein the transit time is given by a predefined value.

Item 81. The method of item 79, further comprising: calculating the transit time based on a difference in fluid pressure between the locations of the reference sensor (4a-4c) and the primary pressure wave sensor (4a-4c).

Item 82. The method of item 77, wherein the reference sensor is an ECG sensor.

Item 83. The method of any one of items 77-81, wherein the primary timing data is obtained by: identifying a set of candidate heart pulses in the monitoring signal or the reference signal; deriving a sequence of candidate time points based on the set of candidate heart pulses; validating the sequence of candidate time points against a temporal criterion; and calculating the timing data as a function of the thus-validated sequence of candidate time points.

Item 84. The method of any one of items 70-83, wherein said calculating the parameter value comprises: generating secondary timing data based on the beat classification data, the secondary timing data representing the occurrence times of the heart pulses for use in calculating the parameter value.

Item 85. The method of item 84, further comprising: generating the secondary timing data, if the beat classification data identifies heart pulses originating from ectopic heart beats and if a selection criterion is met, by estimating a corrected time point for each heart pulse that is classified as originating from an ectopic heart beat.

Item 86. The method of item 85, wherein the selection criterion indicates that the parameter value is at least one of heart rate and heart rate variability.

Item 87. The method of any one of items 84-86, further comprising: processing the secondary timing data for calculation of the parameter value as a measure of at least one of heart rate variability and heart rate. The processing may include calculating the measure of heart rate variability by: at least partly compensating for variations in transit time of the pressure waves originating from the heart beat in the subject, said variations originating from pressure variations in the extracorporeal fluid circuit (20) caused by at least one pumping device (3) in the extracorporeal fluid circuit (20).

Item 88. The method of any one of items 84-87, further comprising, if the beat classification data identifies heart pulses originating from ectopic heart beats: processing the beat classification data and the secondary timing data, for calculation of the parameter value as a measure of heart rate turbulence.

Item 89. The method of any one of items 84-88, further comprising, if the beat classification data identifies heart pulses originating from ectopic heart beats: selecting, based on the beat classification data, a subset of the heart pulses in the monitoring signal and generating the parameter value as a measure of the average temporal shape of the selected subset.

Item 90. The method of item 89, wherein said generating the parameter value comprises: aligning and combining, based on the secondary timing data, the subset of the heart pulses.

Item 91. The method of any one of items 70-90, further comprising, if the beat classification data identifies heart pulses originating from ectopic heart beats: processing the beat classification data for calculation of the parameter value as a count of ectopic heart beats.

Item 92. The method of any one of items 70-91, wherein the measurement data comprises the sequence of heart pulses and at least one interference pulse, and wherein the step of generating the monitoring signal comprises: processing the measurement data to essentially eliminate said at least one interference pulse.

Item 93. The method of item 92, further comprising: obtaining a pulse profile (u(n)) which is a predicted temporal signal profile of the interference pulse, and filtering the measurement data in the time domain, using the pulse profile (u(n)), to essentially eliminate the interference pulse while retaining the sequence of heart pulses.

Item 94. The method of item 93, further comprising: subtracting the pulse profile (u(n)) from the measurement data.

Item 95. The method of item 94, further comprising, before subtracting the pulse profile (u(n)): adjusting at least one of the amplitude, the time scale and the phase of the pulse profile (u(n)) with respect to the measurement data.

Item 96. The method of item 95, further comprising: minimizing a difference between the pulse profile (u(n)) and the measurement data.

Item 97. The method of any one of items 94-96, wherein said at least one interference pulse originates from at least one pumping device (3) in the extracorporeal fluid circuit (20), and wherein said subtracting the pulse profile (u(n)) comprises: obtaining phase information from at least one of: a pump rate sensor (25) coupled to said at least one pumping device (3) and a controller (24) for said at least one pumping device (3); and adjusting a phase of the pulse profile (u(n)) in relation to the measurement data based on the phase information.

Item 98. The method of item 93, further comprising: operating an adaptive filter (160) to generate an estimation signal ($\hat{d}(n)$), based on the pulse profile (u(n)) and an error signal (e(n)) formed as a difference between the measurement data and the estimation signal ($\hat{d}(n)$), such that the adaptive filter (160) essentially eliminates said at least one interference pulse in the error signal (e(n)). The adaptive filter (160) may be operated to generate the estimation signal ($\hat{d}(n)$) as a linear combination of M shifted pulse profiles (u(n)), and specifically the adaptive filter (160) may be operated to linearly combine M instances of the pulse profile (u(n)), which are properly adjusted in amplitude and phase by the adaptive filter (30).

Item 99. The method of item 98, wherein the adaptive filter (160) comprises a finite impulse response filter (162) with filter coefficients that operate on the pulse profile (u(n)) to generate the estimation signal ($\hat{d}(n)$), and an adaptive algorithm (164) which optimizes the filter coefficients as a function of the error signal (e(n)) and the pulse profile (u(n)).

Item 100. The method of item 98 or 99, further comprising: controlling the adaptive filter (160) to lock the filter coefficients, based on a comparison of the rate and/or amplitude of the heart pulses to a limit value.

Item 101. The method of any one of items 93-100, wherein said at least one interference pulse originates from at least one pumping device (3) in the extracorporeal fluid circuit (20), wherein said method further comprises, in a reference measurement: causing said at least one pumping device (3) to generate at least one interference pulse, and obtaining the pulse profile (u(n)) from a reference signal generated by a reference sensor (4a-4c).

Item 102. The method of item 101, further comprising: operating said at least one pumping device (3) to generate a sequence of interference pulses during the reference measurement, wherein said obtaining the pulse profile (u(n)) comprises: identifying and combining a set of interference pulses in the reference signal.

Item 103. The method of item 101 or 102, further comprising: intermittently effecting the reference measurement to update the pulse profile (u(n)) during operation of the extracorporeal fluid circuit (20).

Item 104. The method of any one of items 93-100, wherein said at least one interference pulse originates from at least one pumping device (3) in the extracorporeal fluid circuit (20), wherein the pulse profile (u(n)) is obtained based on a predetermined signal profile.

Item 105. The method of item 104, further comprising: modifying the predetermined signal profile according to a mathematical model based on a current value of one or more system parameters of the extracorporeal fluid circuit (20).

Item 106. The method of item 93-100, wherein said at least one interference pulse originates from at least one pumping device (3) in the extracorporeal fluid circuit (20), wherein said obtaining the pulse profile (u(n)) comprises: obtaining a current value of one or more system parameters of the extracorporeal fluid circuit (20), and obtaining the pulse profile (u(n)) as a function of the current value.

Item 107. The method of item 106, wherein said obtaining the pulse profile (u(n)) comprises: identifying, based on the current value, one or more temporal reference profiles ($r_1(n)$, $r_2(n)$) in a reference database (DB); and obtaining the pulse profile (u(n)) based on said one or more temporal reference profiles ($r_1(n)$, $r_2(n)$).

Item 108. The method of item 107, wherein said one or more system parameters is indicative of a pumping rate of said at least one pumping device (3).

Item 109. The method of item 107 or 108, wherein each temporal reference profile ($r_1(n)$, $r_2(n)$) in the reference database (DB) is obtained by a reference measurement in the extracorporeal fluid circuit (20) for a respective value of said one or more system parameters.

Item 110. The method of item 106, wherein said obtaining the pulse profile (u(n)) comprises: identifying, based on the current value, one or more combinations of energy and phase angle data in a reference database (DB); and obtaining the pulse profile (u(n)) based on said one or more combinations of energy and phase angle data.

Item 111. The method of item 110, wherein said obtaining the pulse profile (u(n)) comprises: combining a set of sinusoids of different frequencies, wherein the amplitude and phase angle of each sinusoid is given by said one or more combinations of energy and phase angle data.

Item 112. The method of item 106, wherein said obtaining the pulse profile (u(n)) comprises: inputting the current value into an algorithm which calculates the response of the primary pressure wave sensor (4a-4c) based on a mathematical model of the extracorporeal fluid circuit (20).

Item 113. The method of item 92, further comprising: obtaining a pulse profile (u(n)) which is a predicted temporal signal profile of the heart pulse, and filtering the measurement data in the time domain, using the pulse profile (u(n)), to essentially eliminate the interference pulse while retaining the sequence of heart pulses.

Item 114. The method of item 113, further comprising: operating an adaptive filter (160) to generate an estimation signal ($\hat{d}(n)$), based on the pulse profile (u(n)) and an error signal (e(n)) formed as a difference between the measurement data and the estimation signal ($\hat{d}(n)$), such that the adaptive filter (160) essentially eliminates said at least one interference pulse in the estimation signal ($\hat{d}(n)$). The adaptive filter (160) may be operated to generate the estimation signal ($\hat{d}(n)$) as a linear combination of M shifted pulse profiles (u(n)), and specifically the adaptive filter (160) may be operated to linearly combine M instances of the pulse profiles (u(n)), which are properly adjusted in amplitude and phase by the adaptive filter (30).

Item 115. The method of any one of items 70-114, which comprises a first process for generating the monitoring signal, a second process for obtaining primary timing data, and a third process for calculating the parameter value, wherein the method further comprises: evaluating the magnitude of the heart pulses in the monitoring signal, or in a reference signal obtained from a reference sensor (4a-4c), and selectively controlling at least one of the first, second and third processes based on the magnitude of the heart pulses.

Item 116. The method of any one of items 70-115, wherein the measurement data comprises the sequence of heart pulses and at least one interference pulse, which originates from at least one pumping device (3) in the extracorporeal fluid circuit (20), wherein the method further comprises: calculating a rate of heart pulses in the monitoring signal, or in a reference signal obtained from a reference sensor (4a-4c), and causing a pumping frequency of said at least one pumping device (3) to be controlled in relation to the rate of heart pulses.

Item 117. The method of item 116, wherein the pumping frequency is controlled to shift the rate of interference pulses away from the rate of heart pulses.

Item 118. The method of item 116, wherein the pumping frequency is controlled to synchronize the rate of interference pulses with the rate of heart pulses, while applying a given phase difference between the interference pulses and the heart pulses.

Item 119. The method of any one of items 70-116, wherein the extracorporeal fluid circuit (20) comprises at least one pumping device (3) which, when in an operating state, generates interference pulses in the measurement data, wherein the measurement data is obtained while said at least one pumping device (3) is intermittently set in a disabled state.

Item 120. The method of any one of items 70-119, wherein the cardiovascular property is at least one of an arterial status of the cardiovascular system of the subject, a degree of calcification in the cardiovascular system of the subject, a status of a blood vessel access used for connecting the extracorporeal fluid circuit (20) to the cardiovascular system of the subject, a heart rate variability, a heart rate, a heart rate turbulence, an ectopic beat count, and an origin of ectopic beats.

Item 130. A computer-readable medium comprising computer instructions which, when executed by a processor, cause the processor to perform the method of any one of items 70-120.

The invention claimed is:

1. A device for monitoring a cardiovascular property of a subject, wherein the device comprises:
   a primary pressure wave sensor positioned and arranged to detect pressure waves in an extracorporeal fluid circuit in fluid communication with the cardiovascular system of the subject, the extracorporeal fluid circuit including a venous line and an arterial line; and
   an input configured to obtain measurement data from the primary pressure wave sensor,
   wherein the device further comprises a signal processor configured to:
   generate a time-dependent monitoring signal based on the measurement data, such that the monitoring signal comprises a sequence of heart pulses, wherein each heart pulse represents a pressure wave originating from a heart beat in the subject;
   determine beat classification data for each heart pulse in the monitoring signal, the beat classification data including information sufficient to distinguish between heart pulses originating from normal heart beats and heart pulses originating from ectopic heart beats;
   form a classification of at least one heart pulse of the sequence of heart pulses using the beat classification data, the classification based on (i) the at least one heart pulse represented as a cluster of shape features, and (ii) distances of the at least one heart pulse cluster of shape features from a plurality of clusters of shaped features of other heart pulses, wherein each cluster is in an N-dimensional space, and wherein N represents a number of shape features for each heart pulse;

calculate, based at least partly on the classification of the at least one heart pulse, a parameter value indicative of the cardiovascular property; and at least one of (i) cause the calculated parameter value to be displayed, or (ii) generate an alarm based on the calculated parameter value.

2. The device of claim 1, wherein the beat classification data includes information sufficient to distinguish between different types of ectopic heart beats.

3. The device of claim 1, wherein the signal processor is configured to determine the beat classification data based on at least one of primary timing data, which represents an occurrence time of each heart pulse in the monitoring signal, and shape data, which represents a shape of each heart pulse in the monitoring signal.

4. The device of claim 3, wherein the signal processor is configured to determine the beat classification data by processing the monitoring signal to extract at least one shape feature which is representative of temporal shape of each heart pulse.

5. The device of claim 3, wherein the signal processor is configured to determine the beat classification data based on a combination of a plurality of different shape features extracted from each heart pulse.

6. The device of claim 3, wherein the signal processor is configured to determine the beat classification data by extracting at least part of a temporal profile of each heart pulse, and matching said at least part of the temporal profile against a set of templates.

7. The device of claim 3, wherein the signal processor is configured to determine the beat classification data by obtaining, based on the primary timing data, time differences between heart pulses in the monitoring signal, and evaluating each time difference against a time interval criterion.

8. The device of claim 1, wherein the signal processor is configured to calculate the parameter value by generating secondary timing data based on the beat classification data, the secondary timing data representing occurrence times of the at least one heart pulse for use in calculating the parameter value.

9. The device of claim 8, wherein the signal processor is configured to, if the classification identifies heart pulses originating from ectopic heart beats and if a selection criterion is met, generate the secondary timing data by estimating a corrected time point for each heart pulse that is classified as originating from an ectopic heart beat.

10. The device of claim 9, wherein the selection criterion indicates that the parameter value is at least one of heart rate and heart rate variability.

11. The device of claim 8, wherein the signal processor is configured to process the secondary timing data for calculation of the parameter value as a measure of at least one of heart rate variability and heart rate.

12. The device of claim 8, wherein the signal processor is configured to, if the classification identifies heart pulses originating from ectopic heart beats, process the beat classification data and the secondary timing data, for calculation of the parameter value as a measure of heart rate turbulence.

13. The device of claim 8, wherein the signal processor is configured to, if the classification identifies heart pulses, originating from ectopic heart beats, select, based on the beat classification data, a subset of the heart pulses in the monitoring signal and to generate the parameter value as a measure of an average temporal shape of the selected subset.

14. The device of claim 13, wherein the signal processor is configured to generate the average temporal shape by aligning and combining, based on the secondary timing data, the subset of the heart pulses.

15. The device of claim 1, wherein the signal processor is configured to, if the classification identifies heart pulses originating from ectopic heart beats, process the beat classification data for calculation of the parameter value as a count of ectopic heart beats.

16. The device of claim 1, wherein the measurement data comprises the sequence of heart pulses and at least one interference pulse, wherein the signal processor is configured to generate the monitoring signal by processing the measurement data to essentially eliminate said at least one interference pulse.

17. The device of claim 16, wherein the signal processor is configured to obtain a pulse profile (u(n)) which is a predicted temporal signal profile of the interference pulse, and to filter the measurement data in the time domain, using the pulse profile (u(n)), to essentially eliminate the interference pulse while retaining the sequence of heart pulses.

18. The device of claim 1, wherein the signal processor implements a first process for generating the monitoring signal, and a second process for obtaining primary timing data, and a third process for calculating the parameter value, wherein the signal processor is further configured to evaluate a magnitude of each heart pulse in the monitoring signal, or in a reference signal obtained from a reference sensor.

19. The device of claim 1, wherein the measurement data comprises the sequence of heart pulses and at least one interference pulse, which originates from at least one pumping device in the extracorporeal fluid circuit, wherein the signal processor is further configured to calculate a rate of heart pulses in the monitoring signal, or in a reference signal obtained from a reference sensor, and to cause a pumping frequency of said at least one pumping device to be controlled in relation to the rate of heart pulses.

20. The device of claim 19, wherein the pumping frequency is controlled to shift a rate of interference pulses away from the rate of heart pulses.

21. The device of claim 19, wherein the pumping frequency is controlled to synchronize a rate of interference pulses with the rate of heart pulses, while applying a given phase difference between the at least one interference pulse and the sequence of heart pulses.

22. The device of claim 1, wherein the cardiovascular property is at least one of an arterial status of the cardiovascular system of the subject, a degree of calcification in the cardiovascular system of the subject, a status of a blood vessel access used for connecting the extracorporeal fluid circuit to the cardiovascular system of the subject, a heart rate variability, a heart rate, a heart rate turbulence, an ectopic beat count, and an origin of ectopic beats.

23. The device of claim 1, further comprising the extracorporeal fluid circuit including at least one pumping device which, when in an operating state, generates interference pulses in the measurement data, wherein the input is configured to obtain the measurement data while said at least one pumping device is intermittently set in a disabled state.

24. The device of claim 1, wherein the at least one heart pulse of the sequence of heart pulses is classified based on a nearest cluster of heart pulses in the N-dimensional space.

25. The device of claim 1, wherein the alarm is an audible, visual or tactile alarm or warning signal based on the calculated parameter value.

26. A device for monitoring a cardiovascular property of a subject, said device comprising:
- a primary pressure wave sensor positioned and arranged to detect pressure waves in an extracorporeal fluid circuit which is connected in fluid communication with the cardiovascular system of the subject, the extracorporeal fluid circuit including a venous line and an arterial line;
- a data analysis part for
    - determining a time-dependent monitoring signal based on measurement data obtained from the primary pressure wave sensor, such that the monitoring signal comprises a sequence of heart pulses, wherein each heart pulse represents a pressure wave originating from a heart beat in the subject;
    - determining beat classification data for each heart pulse in the monitoring signal, the beat classification data including information sufficient to distinguish between heart pulses originating from normal heart beats and heart pulses originating from ectopic heart beats;
    - forming a classification of at least one heart pulse of the sequence of heart pulses using the beat classification data, the classification based on (i) the at least one heart pulse represented as a cluster of shape features, and (ii) distances of the at least one heart pulse cluster of shape features from a plurality of clusters of shaped features of other heart pulses, wherein each cluster is in an N-dimensional space, and wherein N represents a number of shape features for each heart pulse; and
    - calculating, based at least partly on the classification of the at least one heart pulse, a parameter value indicative of the cardiovascular property; and
- at least one of (i) a display for causing the calculated parameter value to be displayed or (ii) an alarm configured to generate an alarm signal based on the calculated parameter value.

27. The device of claim 26, wherein the at least one heart pulse of the sequence of heart pulses is classified based on a nearest cluster of heart pulses in the N-dimensional space.

28. The device of claim 26, wherein the alarm is an audible, visual or tactile alarm or warning signal based on the calculated parameter value.

29. A method for monitoring a cardiovascular property of a mammalian subject, said method comprising:
- obtaining, via a processor, measurement data from a primary pressure wave sensor which is arranged to detect pressure waves in an extracorporeal fluid circuit which is in fluid communication with the cardiovascular system of the subject, the extracorporeal fluid circuit including a venous line and an arterial line;
- generating, via the processor, a time-dependent monitoring signal based on the measurement data, such that the monitoring signal comprises a sequence of heart pulses, wherein each heart pulse represents a pressure wave originating from a heart beat in the subject;
- determining, via the processor, beat classification data for each heart pulse in the monitoring signal, the beat classification data including information sufficient to distinguish between heart pulses originating from normal heart beats and heart pulses originating from ectopic heart beats;
- forming a classification of at least one heart pulse of the sequence of heart pulses using the beat classification data, the classification based on (i) the at least one heart pulse represented as a cluster of shape features, and (ii) distances of the at least one heart pulse cluster of shape features from a plurality of clusters of shaped features of other heart pulses, wherein each cluster is in an N-dimensional space, and wherein N represents a number of shape features for each heart pulse;
- calculating, via the processor, based at least partly on the classification of the at least one heart pulse, a parameter value indicative of the cardiovascular property; and
- at least one of (i) causing the calculated parameter value to be displayed, or (ii) generating an alarm based on the calculated parameter value.

30. A non-transitory computer-readable medium comprising computer instructions which, when executed by the processor, cause the processor to perform the method of claim 29.

31. The method of claim 29, wherein the at least one heart pulse of the sequence of heart pulses is classified based on a nearest cluster of heart pulses in the N-dimensional space.

32. The method of claim 29, wherein the alarm is an audible, visual or tactile alarm or warning signal based on the calculated parameter value.

* * * * *